(12) United States Patent
Dunne (10) Patent No.: US 7,067,493 B2
(45) Date of Patent: *Jun. 27, 2006

(54) SINGLE DOSE AZITHROMYCIN (75) Inventor: Michael W. Dunne, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/172,012

(22) Filed: Jun. 29, 2005

(65) Prior Publication Data
US 2005/0250712 A1 Nov. 10, 2005

Related U.S. Application Data (63) Continuation of application No. 10/628,102, filed on Jul. 25, 2003, now Pat. No. 6,987,093, which is a continuation of application No. 10/224,902, filed on Aug. 21, 2002, now abandoned.

(60) Provisional application No. 60/313,867, filed on Aug. 21, 2001.

(51) Int. Cl.
A01N 43/04 (2006.01)
A61K 31/70 (2006.01)

(52) U.S. Cl. .................................................. 514/29
(58) Field of Classification Search .................. 514/29
See application file for complete search history.

(56) References Cited

U.S. PATENT DOCUMENTS

| 4,328,334 | A | 5/1982 | Kobrehel et al. | |
|---|---|---|---|---|
| 4,474,768 | A | 10/1984 | Bright | |
| 4,517,359 | A | 5/1985 | Kobrehel et al. | |
| 4,963,531 | A | 10/1990 | Remington | |
| 5,498,699 | A | 3/1996 | Djokic et al. | |
| 5,605,889 | A | 2/1997 | Curatolo et al. | |
| 5,633,006 | A | 5/1997 | Catania et al. | |
| 5,686,587 | A | 11/1997 | Yang | |
| 6,068,859 | A | 5/2000 | Curatolo et al. | |
| 6,110,965 | A | 8/2000 | Lazarevski et al. | 514/459 |
| 6,268,489 | B1 | 7/2001 | Allen et al. | |
| 6,569,443 | B1 | 5/2003 | Dawson et al. | 424/483 |
| 2004/0053264 | A1 | 3/2004 | Park | 435/6 |

OTHER PUBLICATIONS

Block et al., "Single Dose Azithromycin (30 mg/kg) in Acute Otitis Media", 38th Annual Meeting of the Infectious Disease Society of America, New Orleans, La., Sep. 7-10, 2000.*

Schonwald, S., et al., Infection, Germany, vol. 27, No. 3, May 1999, pp. 198-202 XP008018295.
Amsden, G.W., et al., The J. of Antimicrobial Chemotherapy, 47(1), pp. 61-66 (2001) XP001159703.
Block, S., et al., 38th Annual Meeting of the Infectious Diseases Society of America, New Orleans, LA, Sep. 7-10, 2000, Single-Sose Azithromycin (30mg/kg) in Acute Otitis Media, Abstract 174.
Muller O., The J. of Antimicrobial Chemotherapy, England, Jun. 1993, vol. 31, suppl. E, Jun. 1993, pp. 137-146 XP008018300.
Nightingale C.H., et al., J. of Infectious Disease Pharmacotherapy 1999, vol. 4, No. 1, pp. 17-24 XP008018297.
Aoki N., Japanese Journal of Chemotherapy 1995, Japan, vol. 43, No. Suppl 6, pp. 234-238 XP008018296.
Morris, D.L., et al., vol. 10, No. 10., Oct. 1991, pp. 859-861, European J. of Clinical Microbiology & Infectious Diseases: Official Publication of the European Society of Clinical Microbiology, Germany XP008018299.
Klepser, M., et al., International J. of Antimicrobial Agents, vol. 17, No. Supp 1, Jun. 2001, p. S157, 22nd International Congress of Chemotherapy; Amsterdam, Jun. 30-Jul. 3, 2001 XP002244592.
Bergogne-Berezin Eugenie, Pathologie Biologie, vol. 43, No. 6, 1995, pp. 498-504, "Azithromycin: Tissue pharmacokinetic data" XP008018308.
Law et al., The Annals of Pharmacotherapy, vol. 38, pp. 433-439, Mar., 2004, "Single-Dose Azithromycin for Respiratory Tract Infections".
Arguedas, A., Single-Dose Therapy In Otitis Media, Poster Presentation at 9th European Congress of Clinical Microbiology and Infectious Diseases, Berlin, Germany, Mar. 21-24, 1999, Clin. Microbiol. Infect. 1999:5 (Supp. 3 Mar.):28 (Abstr).
P/S/L Consulting Group Inc., Single-Dose Zithromax (Azithromycin) as Effective as 10 Days of Augmentin (Amoxcillin/Clavulenate) for Otitis Media, Doctor's Guide; Sep. 14, 2000.
FDA Briefing Package: Zithromax® (Azithromycin) Oral Suspension Single-Dose and Three Day Treatment of Acute Otitis Media, Anti-Infective Drugs Advisory Committee, Nov. 7, 2001.

* cited by examiner

Primary Examiner—Shaojia Anna Jiang
Assistant Examiner—Traviss C. McIntosh, III
(74) Attorney, Agent, or Firm—Peter C. Richardson; Gregg C. Benson; Lance Y. Liu (57) ABSTRACT The present invention relates to a method of treating infections in humans by administering a single dose of azithromycin.

18 Claims, 5 Drawing Sheets

SINGLE DOSE AZITHROMYCIN

This application is a continuation of U.S. patent application Ser. No. 10/628,102, filed on Jul. 25, 2003, now U.S. Pat. No. 6,987,093 which is a continuation of U.S. patent application Ser. No. 10/224,902, filed on Aug. 21, 2002, now abandoned, which in turn is a continuation-in-part of U.S. Patent Application 60/313,867, filed Aug. 21, 2001, which are hereby incorporated by reference herein in their entirety.

FIELD OF THE INVENTION

The present invention relates to a method of treating infection by administering a single dosage of azithromycin.

BACKGROUND OF THE INVENTION

Azithromycin is the U.S.A.N. (generic name) for 9a-aza-9a-methyl-9-deoxo-9a-homoerythromycin A, a broad spectrum antimicrobial compound derived from erythromycin A. Azithromycin was independently discovered by Bright, U.S. Pat. No. 4,474,768 and Kobrehel et al., U.S. Pat. No. 4,517,359. These patents disclose that azithromycin and certain derivatives thereof possess antibacterial properties and are accordingly useful as antibiotics. Azithromycin may be made, formulated and administered according to procedures described in the following U.S. patents, which are all incorporated herein in their entirety by reference: U.S. Pat. Nos. 6,268,489; 4,963,531; 5,633,006; 5,686,587; 5,605,889; 6,068,859; 4,328,334; and 5,498,699.

Azithromycin is administered for the treatment of infections, particularly respiratory infections, more particularly respiratory infections of the bronchial tract, lungs, and sinus, and still more particularly acute otitis media. Acute otitis media is an inflammation of the area behind the eardrum (tympanic membrane) in the chamber called the middle ear. Acute otitis media is an infection that produces pus, fluid, and inflammation within the middle ear.

Acute otitis media may be caused by a variety of pathogens, such as *M. catarrhalis, S. pneumoniae,* and *H. influenzae*. Acute otitis media is particularly common in infants and children. Azithromycin has been prescribed for the treatment of acute otitis media with a 30 mg/kg body weight total treatment dose given as a five day regimen in the US and as a three day regimen in Europe. The multiple dosages prescribed to completely cure the infection have caused compliance problems, particularly in pediatric patients. Even in the adult population, compliance with multiple dosaging regimens is not complete because of forgetfulness and other reasons. A method of treating and curing infection, particularly a microbial infection such as acute otitis media, by administering a single dose of azithromycin would significantly shorten courses of therapy and be of a great advantage to patient compliance.

A continual problem with antibiotic therapy is the emergence of resistant microbial strains. A method of treating microbial infections with a reduced risk of developing treatment-resistant strains is desirable. It is believed that a single dose azithromycin treatment provides such as reduced risk. The inflammatory cells provide a mode of transport of azithromycin to the infection site and provide a reservoir for azithromycin at the infection site. As a result, azithromycin is characterized by high and sustained concentrations in a wide range of tissues, and a particularly increased concentration at sites of infection. It is believed that a single dose therapy with azithromycin, by providing a higher initial concentration at the infection site, may help prevent less susceptible sub-populations of the pathogens initially present from becoming established. Also, a single-dose regimen will result in greater patient compliance, which should contribute to reduced emergence of less susceptible strains.

A related resistance problem is the problem of treating infection caused by pathogens having a high susceptibility threshold to most therapeutically available antiinfective agents. Such resistant pathogens are characterized by being unlikely to be inhibited if the antimicrobial compound reaches the concentrations usually achievable and other therapy is needed. Often, the other therapy involves anti-infective agents with undesirable side effects, such as severe gastrointestinal distress or heightened sensitivity to sun. It is an ongoing problem to develop new therapies to treat disorders caused by such pathogens that exhibit resistance to available anti-infective agents while minimizing undesirable side-effects. It is an object of the present invention to solve these problems with a well-tolerated therapy of a sufficient dosage of azithromycin administered as a single dose to treat infections caused by certain resistant pathogens.

Single dose administration of azithromycin for the treatment of non-gonococcal urethritis and cervicitis due to *C. trachomatis* has been prescribed and is a therapy approved by the US Food and Drug Administration. Single dose treatment of respiratory infections in humans with azithromycin has been reported. For example, Stan Block et al. reported on a study in which a single dose of azithromycin (30 mg/kg) was administered to treat acute otitis media in infants and children six months to twelve years of age. S. Block et al., "Single-Dose Azithromycin (30 mg/kg) in Acute Otitis Media", 38th Annual Meeting of the Infectious Diseases Society of America, New Orleans La., Sept. 7–10, 2000 [Abstract 174]. Arguedas reported on single-dose therapy in otitis media using azithromycin in infants and children. Arguedas, A., "Single-dose therapy in otitis media", Poster Presentation at 9th European Congress of Clinical Microbiology and Infectious Diseases, Berlin, Germany, Mar. 21–24, 1999, *Clin. Microbiol. Infect.* 1999:5 (Supp. 3 March):28 (Abstr). A single oral dose of 2 g azithromycin was administered to healthy male subjects in tests of gastrointestinal side effects reported in U.S. Pat. No. 6,068,859.

SUMMARY OF THE INVENTION

The present invention provides a method of treating a respiratory infection in a human comprising administering to a human in need thereof a single dose of azithromycin wherein the dose is about 30 mg/kg body weight or greater. In another embodiment, the invention is directed to a method of treating a respiratory infection in a human comprising administering to a human in need thereof a single dose of azithromycin wherein the dose is within the range of about 0.15 to 4.5 g.

A further embodiment is directed to a method of treating a respiratory infection caused by *S. pneumoniae* isolates in a human comprising administering to a human in need thereof a single dose of azithromycin. A further embodiment involves the treatment of a respiratory infection in a human in which the respiratory infection is caused by an *S. pneumoniae* isolate containing a mef A gene. In yet another embodiment, the invention is directed to a method of treating a respiratory infection caused by *H. influenzae* in a human comprising administering to a human in need thereof a single dose of azithromycin. A further embodiment is directed to a method of treating an infection caused by *S.*

*pyogenes* in a human comprising administering to a human in need thereof a single dose of azithromycin. In a still further embodiment, the invention is directed to a method of treating an infection caused by *E. faecalis* in a human comprising administering to a human in need thereof a single dose of azithromycin. The invention is also directed to a method of treating a respiratory infection caused by *M. catarrhalis* in a human comprising administering to a human in need thereof a single dose of azithromycin.

DETAILED DESCRIPTION

The invention provides a method of treating infections, particularly respiratory infections such as acute otitis media, in a human in need thereof by administering a single dose of azithromycin. The human patient may be an adult sixteen years of age or older, a child under sixteen years of age, or a young child twelve years of age or younger. By "single dose" is meant a dosage that is administered only once over a 28-day period. The dosage may be administered in a single dosage form, such as one capsule or tablet, or may be divided, e.g. constituted by more than one dosage form, such as by multiple capsules or tablets that are taken at or about the same time. Any type of dosage form may be used, such as capsule, tablet, liquid suspension for oral administration, or liquid for intravenous administration.

The "single dose" of the invention is formulated for immediate release and is not formulated for controlled, sustained or delayed release. For example, an orally administered azithromycin single dose administered according to the present invention is preferably in a form such that it releases azithromycin to the human gastrointestinal tract at a rate such that the total amount of azithromycin released therein is more than 4 mg of azithromycin per kg of patient weight in the first fifteen minutes after ingestion and more preferably is more than 30 mg of azithromycin per kg of weight in the first six hours after ingestion.

Azithromycin can be employed in its pharmaceutically acceptable salts and also in anhydrous as well as hydrated forms, such as the di- and mono-hydrates. All such forms are within the scope of this invention. The azithromycin employed is preferably the dihydrate, which is disclosed in published European Patent Application 0 298 650 A2.

Under the inventive methods, respiratory infections in humans are treated by administering azithromycin in a single dose of about 30 mg/kg body weight or greater.

Preferably, the single dose is between about 30 mg/kg and 90 mg/kg. Other preferred dosages are between about 30 mg/kg and 35 mg/kg body weight, between about 31 mg/kg and 35 mg/kg body weight, between about 35 mg/kg and 40 mg/kg body weight, between about 40 mg/kg and 45 mg/kg body weight, between about 45 mg/kg and 50 mg/kg body weight, between about 50 mg/kg and 55 mg/kg body weight, between about 55 mg/kg and 60 mg/kg body weight, between about 60 mg/kg and 65 mg/kg body weight, between about 65 mg/kg and 70 mg/kg body weight, between about 70 mg/kg and 75 mg/kg body weight, between about 75 mg/kg and 80 mg/kg body weight, between about 80 mg/kg and 85 mg/kg body weight, and between about 85 mg/kg and 90 mg/kg body weight.

Other preferred doses are the following doses: 31 mg/kg or greater, 32 mg/kg or greater, 33 mg/kg or greater, 34 mg/kg or greater, 35 mg/kg or greater, 36 mg/kg or greater, 37 mg/kg or greater, 38 mg/kg or greater, 39 mg/kg or greater, 40 mg/kg or greater, 41 mg/kg or greater, 42 mg/kg or greater, 43 mg/kg or greater, 44 mg/kg or greater, 45 mg/kg or greater, 46 mg/kg or greater, 47 mg/kg or greater, 48 mg/kg or greater, 49 mg/kg or greater, 50 mg/kg or greater, 51 mg/kg or greater, 52 mg/kg or greater, 53 mg/kg or greater, 54 mg/kg or greater, 55 mg/kg or greater, 56 mg/kg or greater, 57 mg/kg or greater, 58 mg/kg or greater, 59 mg/kg or greater, 60 mg/kg or greater, 61 mg/kg or greater, 62 mg/kg or greater, 63 mg/kg or greater, 64 mg/kg or greater, 65 mg/kg or greater, 66 mg/kg or greater, 67 mg/kg or greater, 68 mg/kg or greater, 69 mg/kg or greater, 70 mg/kg or greater, 71 mg/kg or greater, 72 mg/kg or greater, 73 mg/kg or greater, 74 mg/kg or greater, 75 mg/kg or greater, 76 mg/kg or greater, 77 mg/kg or greater, 78 mg/kg or greater, 79 mg/kg or greater, 80 mg/kg or greater, 81 mg/kg or greater, 82 mg/kg or greater, 83 mg/kg or greater, 84 mg/kg or greater, 85 mg/kg or greater, 86 mg/kg or greater, 87 mg/kg or greater, 88 mg/kg or greater, 89 mg/kg or greater, and about 90 mg/kg.

In another embodiment, the single dose of azithromycin is administered as a single dose within the range of about 0.15 to 4.5 g, preferably a dose within the range of about 0.15 to 1.5 g or about 1.5 to 4.5 g. Other preferred doses are a single dose within the range of about 0.7 to 1.5 g, a single dose within the range of about 1.5 to 2.5 g, a single dose within the range of about 2.5 to 3.5 g, and a single dose within the range of about 3.5 to 4.5 g. In other embodiments, the single dose is selected from the group consisting of 0.15, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, and 4.5 g.

The methods of the invention may be used to treat infections caused or mediated by different pathogens. Preferably, the pathogen is selected from *S. aureaus, S. pneumoniae, H. influenzae, M. catarrhalis, E. faecalis,* and *S. pyrogenes,* and more preferably is selected from *S. pneumoniae* isolates having a mef A gene, *H. influenzae* and *M. catarrhalis*. The invention preferably is directed to treating a respiratory infection such as acute otitis media caused or mediated in whole or part by one of these specified pathogens.

EXAMPLES 1.0 Single Dose Azithromycin Pediatric Test

Azithromycin has a long half-life in infected tissues. On pharmocokinetic grounds, it is not the duration but rather the total dose of azithromycin that is predicted to correlate most closely with clinical efficacy. Craig, W. A., "Postantibiotic effects and the dosing of Macrolides, azalides, and streptogramins", In: Zinner, S. H. et al. (editor) *Expanding Indications for New Macrolides, Azalides, and Streptogramins,* New York: Marel Dekker (1997), pp. 27–38. A study was undertaken to examine the efficacy of a single 30 mg/kg oral dose of azithromycin in the treatment of acute otitis media in children.

A trial was performed using a single 30-mg/kg dose of azithromycin in the treatment of otitis media in pediatric patients. Children six months to twelve years were enrolled if they had symptoms and signs of acute otitis media ("AOM") for less than four weeks and middle ear effusion by acoustic reflectometry. Symptoms necessary for enrollment included ear pain or fullness, discharge from the external auditory canal, decreased hearing or fever. On physical examination they must have had one or more of the following: bulging or marked erythema of the tympanic membrane, loss of the normal light reflex or tympanic membrane landmarks, or impaired tympanic mobility on biphasic pneumatic otoscopy. The, effusion was to be documented by acoustic reflectometry with an abnormal reading of 3 or higher. Patients were excluded if they had a history of hypersensitivity to macrolides or azithromycin, had been treated with antibiotics in the prior thirty days, had symptoms of otitis media for longer than four weeks, had tympanostomy tubes present, or had been receiving antimicrobial prophylaxis.

Samples of middle ear fluid were obtained by tympanocentesis or, in the case of a perforated tympanic membrane, by swab. Middle ear fluid samples were obtained for culture at baseline. Patients then received azithromycin 30 mg/kg as a single dose. Children who vomited within thirty minutes of dosing were redosed.

Samples of middle ear fluid were split for storage at a central laboratory and cultured locally. All pathogens isolated locally were subcultured and sent to a central laboratory for confirmation and susceptibility testing, performed by Kirby-Bauer disk-diffusion or MIC testing according to NCCLS standards.

Polymerase chain reaction (PCR) determination of resistance mechanisms in all the azithromycin-resistant pneumococci was done.

A phone contact occurred on study day 5 to assess for adverse events followed by visits on days 10 and 24–28, at which time detailed clinical assessments were made and adverse events were recorded. Definitions included clinical cure (complete resolution of all signs and symptoms of AOM); improvement (partial resolution of signs and symptoms); or failure (no change or worsening of signs and symptoms, or requirement for additional antibiotic therapy for AOM). Any patient considered to have failed therapy was to have a repeat tympanocentesis.

Statistical Methodology

The primary endpoint of the trial was the investigator designated cure rate at Day 24–28 for which a 95%. confidence interval was computed using the normal approximation to the binomial distribution. Other endpoints analyzed included the clinical response rate by baseline pathogen at Day 24–28, the overall clinical response at Day 10, the percentage of subjects with individual signs and symptoms, as well as findings from pneumatic otoscopy and acoustic reflectometry. Only *Streptococcus pneumoniae, Moraxella catarrhalis* and *Haemophilus influenzae* were considered baseline pathogens for the purposes of these analyses.

Results

This trial was an open-label, non-comparative study conducted at twenty-two sites from the United States, Costa Rica, Guatemala and Chile.

A total of 248 patients were entered into the trial of whom 247 received azithromycin. Children were enrolled from sites in the United States (63%), Costa Rica (16%), Guatemala (13%) and Chile (8%). The mean age of the children was 3.4 years (range 6 months–12 years). Seventy-two percent (178/248) of the children were noted to have had previous episodes of otitis media and eight percent reported a history of sinusitis. The mean duration of symptoms related to the present episode of acute otitis media was 2.5 days.

The clinical cure rate, as determined by the investigator, at day 24–28 was 206/242 (85%) (table 1). Children less than two years of age had a somewhat lower cure rate (64/83; 77%) while those greater than two years of age were somewhat more likely to be cured (142/159; 89%). Similar results were seen at day 10 with an overall success rate (cure+improvement) of 89% (213/240).

One hundred twenty four patients had a pathogen identified at baseline by culture. The clinical cure rate for these subjects at day 24–28 was 100/124 (81%). Cure rates were highest for patients with *M. catarrhalis* isolated at baseline (10/10; 100%) followed by *S. pneumoniae* (67/76; 88%) and *H. influenzae* (28/44; 64%). At day 10, the clinical success rate for patients with a pathogen identified at baseline was 86% (105/122). Success rates by baseline pathogen were as follows: *M. catarrhalis*—10/10 (100%); *S. pneumoniae*—70/76 (92%); *H. influenzae*—30/42 (71%).

Figure 1:
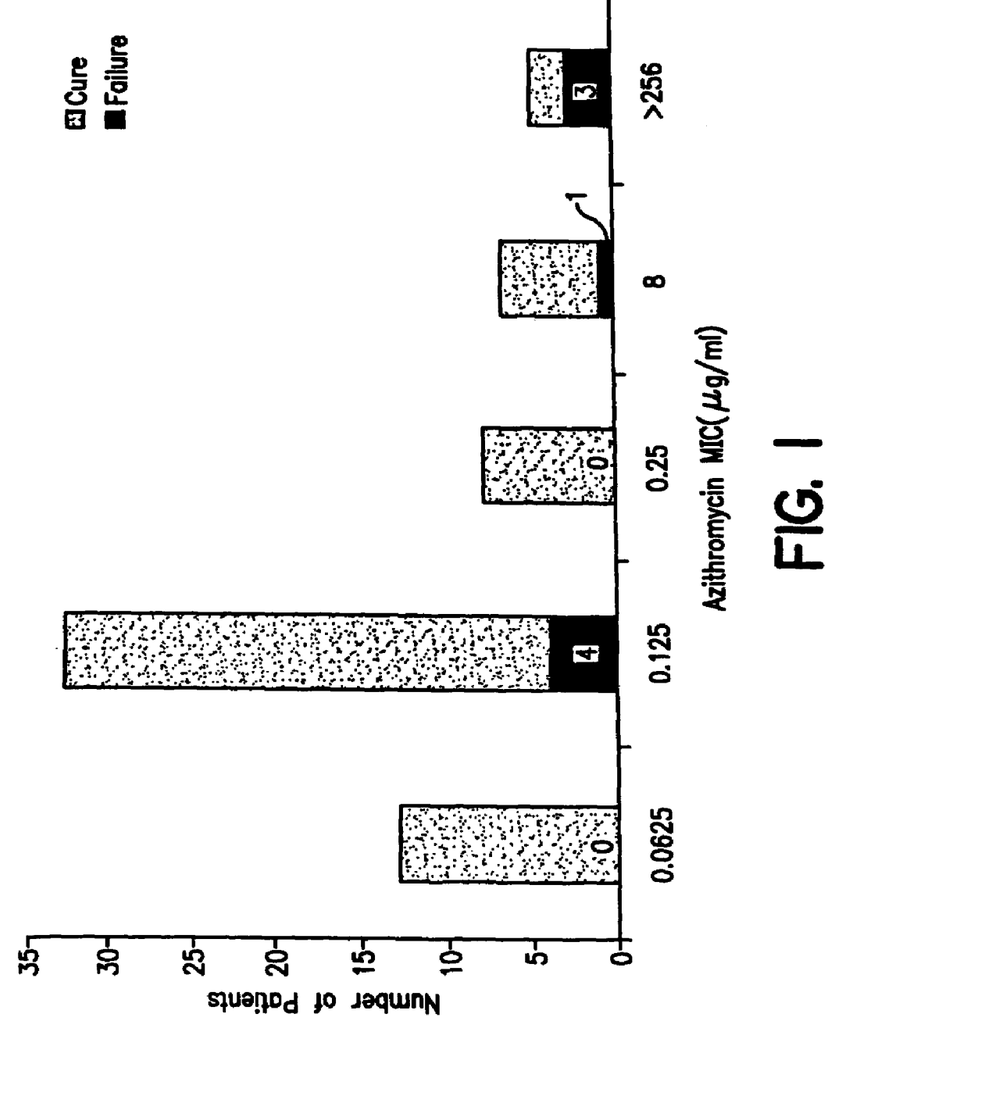
FIG. 1 shows Day 28 Outcome and MIC Distribution for azithromycin. Baseline susceptibility data for azithromycin was available for 66 subjects with *S. pneumonia* who had a clinical outcome on day 28. Clinical cure is shown in gray and clinical failures in black. Isolates with an MIC of 8 µl/ml to azithromycin contained the mef A gene and isolates with an MIC>256 µl/ml contained the erm B gene.

All *H. influenzae* and *M. catarrhalis* that were isolated were susceptible to azithromycin. Twelve children were found to have an infection with an isolate of *S. pneumoniae* resistant to macrolides (FIG. 1). Five of the 12 isolates had an MIC of >256 µg/ml. All five isolates were resistant to clindamycin and on PCR were found to contain the erm B gene. Only two of these five patients were cured at day 28. The seven remaining isolates had an MIC of 8 µg/ml, were sensitive to clindamycin and were found to contain the mef A gene. Six of these seven patients were cured at day 28. The patient who failed was resolving the disease in the ear from which the baseline isolate was obtained but had a different *S. pneumoniae* isolate recovered on day 4 from the opposite ear. This second isolate had an MIC of >256 µg/ml, was resistant to clindamycin and contained the erm B gene. The two isolates also differed by pulsed field electrophoresis. Nine children had isolates of *S. pneumoniae* that were penicillin resistant (MIC>2 µg/ml). Clinical cure at day 28 was seen in 6 of these children. The 3 children who failed therapy had isolates with an MIC>256 µg/ml to macrolides and contained the erm B gene.

Ninety-two percent of patients had complete resolution of their baseline symptoms by day 28. Tympanic membrane motility was impaired in 93% of patients at baseline, decreasing to 27% by day 10 and 12% at day 24–28. Other objective signs of tympanic membrane disease were seen in less than 10% of subjects at day 24–28. Abnormal acoustic reflectometry scores were seen in 214/233 (92%) of patients at baseline. By day 24–28 completely normal readings were found in 53% of children with 83% having scores improved from baseline.

Adverse events were noted in 30/248 (12.1%) subjects possibly or probably related to azithromycin. Most common adverse events were vomiting (6%) and diarrhea (3%).

Discussion

The results of this study demonstrate that treatment of children with otits media with a single oral dose of azithromycin was well tolerated and resulted in adequate presumed pathogen eradication rates. A single dose treatment for acute otitis media could lead to improved compliance. Moreover, azithromycin is believed to be the only oral antimicrobial therapy known at this time that can be delivered in one administration.

Figure 2:
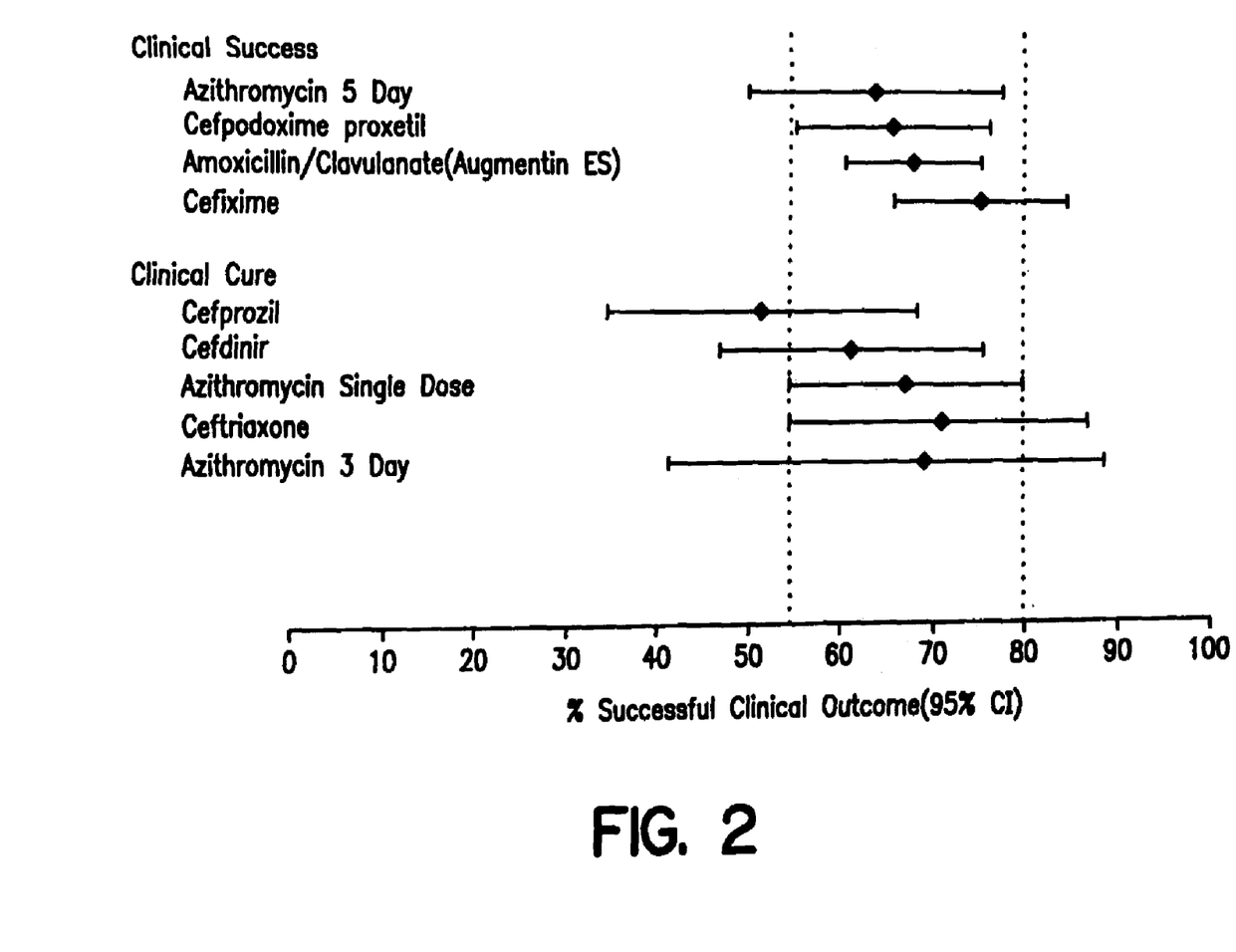
FIG. 2 shows *H. influenzae* Clinical Outcome—Test of Cure Visit day 21–35. Presented are the 95% confidence intervals on the point estimate of success for all drugs approved for treatment of otitis media that had data available in the product label on clinical outcome at day 28 in patients with *H. influenza* identified at baseline. The data is presented as clinical success (cure+improvement) or cure alone as shown in the label. The vertical dashed lines mark the limits of the 95% confidence interval for single dose azithromycin. No attempt was made to adjust outcomes by important demographic variables.

In this study 124/247 (50%) children with AOM had a bacterial pathogen cultured from the tympanic fluid, similar to isolation rates from previous trials. Azithromycin given as a single 30 mg/kg oral dose resulted in clinical cure rates consistent with those observed after a similar total dose was given over five days or over three days. Response rates at day 24–28 for S. pneumoniae and M. catarrhalis are high, and that for H. influenzae is consistent with other similarly designed clinical trials (FIG. 2). On pharmacokinetic grounds this outcome can be explained given that the efficacy of azithromycin is primarily dependent on the total dose delivered, as measured by the $AUC_{24}$, and not the delivery regimen. The amount of drug delivered in the first 24 hours is higher with a single dose regimen compared with either the three day or five day treatment options. While the contribution of Cmax cannot be excluded, it is felt that outcome is likely to be best predicted by $AUC_{24}/MIC$, supporting the overall comparability of these results to the three and five day regimens. Of particular interest was the efficacy in 6/7 patients, whose S. pneumoniae isolates were found to contain the mef A gene, responsible for efflux-mediated resistance. The S. pneumoniae isolates having a mef A gene are known as resistant to macrolides. Azithromycin, which is a macrolide, surprisingly was able to effectively treat infections caused or mediated by S. pneumoniae isolates having a mef A gene when administered as a single dose of 30 mg/kg. The possibility that efflux pump resistance could be overcome by exposing resistant organisms to higher concentrations of drug earlier in the course of therapy was noteworthy.

In conclusion, treatment of acute otitis media with a single oral dose of azithromycin was safe and effective therapy, and it offers a therapeutic alternative that maximizes compliance while minimizing the burden on the patient and the caregiver.

TABLE 1

Clinical Outcome by Age Range and Baseline Pathogen.

|  | Azithromycin | 95% Confidence Interval |
|---|---|---|
| Randomized and treated Day 10 Clinical Success (Cure + Improvement) | 247 | |
| All Subjects | 213/240 (89%) | 85%, 93% |
| Age < 2 years | 69/82 (84%) | 76%, 93% |
| Age > 2 years | 144/158 (91%) | 81%, 96% |
| By pathogen identified at baseline | 105/122 (86%) | |
| S. pneumoniae | 70/76 (92%) | |
| M. catarrhalis | 10/10 | |
| H. influenzae | 30/42 (71%) | |

TABLE 1-continued

Clinical Outcome by Age Range and Baseline Pathogen.

|  | Azithromycin | 95% Confidence Interval |
|---|---|---|
| Day 24–28 Clinical Cure | | |
| All Subjects | 206/242 (85%) | 80%, 90% |
| Age < 2 years | 64/83 (77%) | 68%, 87% |
| Age > 2 years | 142/159 (89%) | 84%, 94% |
| By pathogen identified at baseline | 100/124 (81%) | |
| S. pneumoniae | 67/76 (88%) | |
| M. catarrhalis | 10/10 | |
| H. influenzae | 28/44 (64%) | |

2.0 Single Dose Azithromycin Animal Tests 2.1 Summary

Laboratory experiments with azithromycin suggest that it is the total amount of drug rather than the interval of the drug dosing regimen that determines the concentration at the infection site and results in efficacy (Tables 2 and 3). In the acute murine models challenged with S. pneumoniae, H. influenzae, S. pyogenes, or E. faecalis, azithromycin was superior in efficacy when given as a single oral dose as determined by $PD_{50}$ measurements. A $PD_{50}$ measurement is the protective dose of a drug required to protect 50% of a cohort of animals from death when infected at a lethal level with a given pathogen. These preclinical infection model data are consistent with what is being observed in clinical studies supporting the one-day therapy advantage over a more prolonged course of therapy.

TABLE 2

The Effect of Dose Regimen on Efficacy of Azithromycin and Clarithromycin in an Acute Murine Model

| Pathogen | Drug | MIC (μg/ml) | Dosing Regimen | Oral PD50 (mg/kg/day) |
|---|---|---|---|---|
| S. pyogenes | Azithromycin | 0.06 | 3 days | 3.8 (3.8–3.9) |
|  |  |  | 2 days | 2.5 (1.8–3.3) |
|  |  |  | 1 day | 1.0 (0.6–1.4) |
| S. pyogenes | Clarithromycin | 0.06 | 3 days | 3.1 (2.6–3.7) |
|  |  |  | 2 days | 2.2 (0.9–3.6) |
|  |  |  | 1 day | 11.3 (3.1–19.4) |
| H. influenzae | Azithromycin |  | 3 days | 181.6 (180.1–183.1) |
|  |  |  | 2 days | 49.9 (41.5–58.5) |
|  |  |  | 1 day | 25.3 (14.3–36.2) |
| H. influenzae | Clarithromycin |  | 1 day | >200 |
| E. faecalis | Azithromycin |  | 3 days | 59.3 (27.5–91.2) |
|  |  |  | 2 days | 42.7 (42.2–43.2) |
|  |  |  | 1 day | 14.8 (10.2–19.5) |
| E. faecalis | Clarithromycin |  | 3 days | 18.8 (7.2–30.3) |
|  |  |  | 2 days | 23.7 (5.4–42) |
|  |  |  | 1 day | 2.2 (0.9–4.2) |

It appears that the additional component of Cmax (3-fold better when administered as a single dose vs. the same total dose administered over 3 days) may also factor into the effectiveness of the regimen. The data suggest that Peak/MIC as well as AUC/MIC play important roles in predicting efficacy. Thus, using the same total therapeutic dose, the duration of treatment with azithromycin can be reduced and appears to be more efficacious (Tables 2–6). While AUC/MIC still predicts efficacy, these results reflect the contribution of additional factors, namely Cmax and azithromycin's prolonged persistent effects, on efficacy.

Since inflammatory cells provide a mode of transport to the infection site and a reservoir for azithromycin at the infection site, superior delivery to the infection site is believed to occur when one administers large azithromycin doses as early as practical during the period where maximal inflammation is associated with the infection. The higher initial concentration at the infection site may help prevent less susceptible sub-populations of the pathogens initially present from becoming established. This has been proposed as the reason for less in vivo emergence of resistance to azithromycin compared with clarithromycin in patients who received either drug for treatment or prophylaxis against *M. avium*. A shorter oral dosage regimen would also result in greater patient compliance, which should contribute to reduced emergence of less susceptible strains.

TABLE 3

The Effect of Dose Regimen on Efficacy of Azithromycin and Clarithromycin in Murine Pulmonary Infection Model.

| Pathogen | Drug | MIC (μg/ml) | Dosing Regimen | Oral PD50 (mg/kg/day) |
|---|---|---|---|---|
| S. pneumoniae | Azithromycin | 0.06 | 3 days | 49.4 (28.1–70.8) |
| | | | 2 days | 27.6 (22.8–32.4) |
| | | | 1 day | 20.4 (16.4–24.3) |
| S. pneumoniae | Clarithromycin | 0.06 | 3 days | >200 |
| | | | 2 days | >200 |
| | | | 1 day | >200 |

Figure 3A:
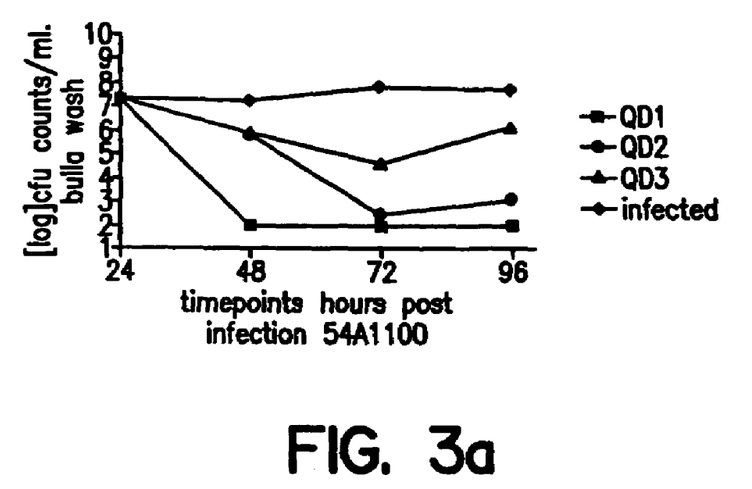
FIGS. 3*a* and 3*b* show the eradication of *H. influenzae* in a gerbil model of middle ear infection.
Figure 3B:
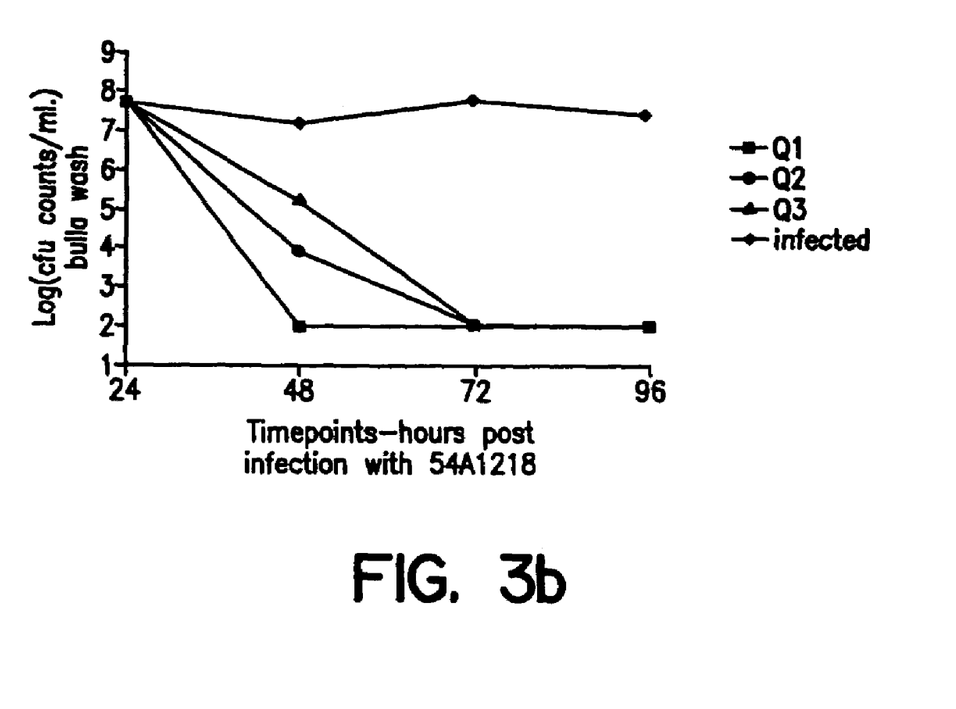

The improvement in the $PD_{50}$ for treatment of *H. influenzae* was especially noteworthy. These findings have been extended to a gerbil model of middle ear infection challenged with two different strains of *H. influenzae* (Table 4 and FIG. 3). *H. influenzae* strains 54A1100 and 54A1218 are non-typable isolates; 54A1218 also carries a TEM-1 β-lactamase. In these experiments, colony-forming units (CFU) are assessed from the bulla wash of five gerbils per time point. The $ED_{50}$ values reflect the dose in which the CFU recoverable from the bulla wash is 50% of the non-treated animals. In the first experiment, azithromycin administered as a single dose was found to be as efficacious as the same total dose given over 2 or 3 days (Table 4).

TABLE 4

The Effect of Dose Regimen on Efficacy of Azithromycin in the Gerbil Middle Ear Infection Model.

| Pathogen | MIC (μg/ml) | Dosing Regimen | ED50 (mg/kg/total) |
|---|---|---|---|
| H. influenzae | 1 | 3 days | 162.9 (140–185.9) |
| | | 2 days | 138.1 (118.7–157.6) |
| | | 1 day | 138.1 (118.7–157.6) |

However, the in vivo kill kinetics demonstrated that the one-day dosing therapeutic regimen resulted in the most rapid eradication of the pathogens (FIG. 3) and, in the case of 54A1100, was the only dosing regimen that leads to complete clearance. Thus, a single dose therapy has advantages over a more prolonged course of therapy.

Several studies have shown good efficacy for azithromycin as compared to other commercial antibiotics. For the localized and intracellular infections, this efficacy correlated with the sustained high tissue levels of azithromycin. Studies of this nature continue to be published. For example, of the several macrolides tested (azithromycin, erythromycin, clarithromycin and roxithromycin), azithromycin was the only one that was efficacious after a single oral 10 mg/kg dose in a *Mycoplasma pneumoniae* pulmonary infection model in hamsters. This efficacy correlated with the high Cmax and prolonged exposure for azithromycin in uninfected lungs compared with other macrolides. In a mouse *Chlamydia trachomatis* salpingitis model, azithromycin (±an anti-inflammatory agent) was superior to doxycycline and ofloxacin combinations in preserving fertility.

A hypothesis to explain the transfer of azithromycin from tissue cells to non-intracellular pathogens growing in contact with the tissue cells has been proposed. Recently, the results from a mouse model demonstrated azithromycin administered as a single dose significantly increased survival versus a pneumococcal challenge compared with all the other dose regimens. This confirmed our studies discussed above. These data suggest that the high initial concentrations of azithromycin favor a good outcome.

2.2 Supporting Data 2.2.1 Murine Lung Infection Model Challenged with *Streptococcus pneumoniae*

Subject

Accelerated dosing study. In vivo evaluation of azithromycin and clarithromycin giving the same total dose over 1, 2 and 3 days vs. an intranasal lung infection produced by a susceptible *Streptococcus pneumoniae* (02J1016) in 21.1 gm CF-1 female mice.

Comments

Azithromycin and clarithromycin are both active against the susceptible *Streptococcus pneumoniae* 02J1016 that produces a more slowly developing disease relative to other pneumococcal strains in the in vivo panel. In this pulmonary infection model 100% mortality in no-drug controls is not observed until 7 days post-infection. Clarithromycin was chosen as a comparator to azithromycin because the pharmacokinetics for these two macrolides are quite different. While clarithromycin achieves relatively high blood levels quickly and is cleared fairly rapidly, azithromycin accumulates in tissues and leeches out slowly over time into the bloodstream yielding overall lower blood levels than clarithromycin but a much longer exposure time. Additionally, the research of Craig et al. in preclinical species suggests that the outcomes observed with azithromycin best correlate with the PD parameter of the AUC/MIC and time above MIC for clarithromycin. We modeled the differences in PK/PD over a longer period. The experiment below was to determine if the compounds work better against a lung infection with *Streptococcus pneumoniae* if the same total dose was given over a 1, 2, or 3-day period administered using a q.d. therapeutic regimen.

Azithromycin performs the best when given once rather than the total dose being spread out over 3 days. It is important to note that while the azithromycin one day dosing $PD_{50}$ (20.4 mg/kg/regimen) is significantly different than the 3 day dosing $PD_{50}$ (49.4 mg/kg/regimen), both are within the 95% confidence limits of the 2 day dosing regimen $PD_{50}$ (27.6 mg/kg/regimen).

Clarithromycin fails ($PD_{50}$>200 mg/kg/regimen) using the q.d. regimen regardless as to the duration of therapy. This is puzzling since clarithromycin has a MIC equivalent to that of azithromycin against 02J1016 (0.01–0.06 ug/ml). However, since clarithromycin is cleared more rapidly from the animal and this infection takes longer to manifest itself and cause mortality, this is most likely an accurate result. Previous efficacy data with clarithromycin in this pneumococcal pneumonia model was generated following BID administration over two days of therapy where clarithromycin therapy is successful with $PD_{50}$s ranging from 5–25 mg/kg.

Procedure

Azithromycin and clarithromycin were administered P.O. in diluent q.d. for 1, 2 or 3 days after an I.N. challenge with *Streptococcus pneumoniae* (02J1016).

| Compound | Dose (mg/kg/day) | Mice Surviving/Total | PD50 (mg/kg/regimen) |
|---|---|---|---|
| Azithromycin P.O. | 33.3 | 9/10 | 49.4 (28.1–70.8)* |
| Lot #17419-64-IF | 8.3 | 1/10 | |
| MIC 0.02–0.13 µg/ml | 2.1 | 0/10 | |
| 3 day regimen | 0.52 | 0/10 | |
| Azithromycin P.O. | 50.0 | 9/10 | 27.6 (22.8–32.4) |
| Lot #17419-64-1F | 12.5 | 4/10 | |
| MIC 0.02–0.13 µg/ml | 3.12 | 0/10 | |
| 2 day regimen | 0.78 | 0/10 | |
| Azithromycin P.O. | 100.0 | 10/10 | 20.4 (16.4–24.3) |
| Lot #17419-64-1F | 25.0 | 7/10 | |
| MIC 0.02–0.13 µg/ml | 6.25 | 1/10 | |
| 1 day regimen | 1.56 | 0/10 | |
| Clarithromycin P.O. | 66.7 | 2/10 | >200 |
| Lot #34844-174-01 | 16.7 | 0/10 | |
| MIC 0.01–0.06 µg/ml | 4.2 | 0/10 | |
| 3 day regimen | 1.04 | 0/10 | |
| Clarithromycin P.O. | 100.0 | 1/10 | >200 |
| Lot #34844-174-01 | 25.0 | 0/10 | |
| MIC 0.01–0.06 µg/ml | 6.25 | 0/10 | |
| 2 day regimen | 1.56 | 0/10 | |
| Clarithromycin P.O. | 200.0 | 4/10 | >200 |
| Lot #34844-174-01 | 50.0 | 1/10 | |
| MIC 0.01–0.06 µg/ml | 12.5 | 1/10 | |
| 1 day regimen | 3.12 | 0/10 | |
| Infected (non-treated) control | | | |
| 10-1 dilution | | 0/10 | |
| 10-2 dilution (used in study) | | 0/10 | |
| 10-3 dilution | | 0/10 | |
| BHI (non-infected control) | | 10/10 | |

*95% confidence limits
Bacterial challenge: $2.88 \times 10^4$ organisms/mouse 2.2.2 Murine Acute Infection Model Challenged with *Streptococcus pyogenes*

Subject

Accelerated dosing study. In vivo evaluation of azithromycin and clarithromycin giving the same total dose over 1, 2 and 3 days vs. an acute infection produced by a susceptible *Streptococcus pyogenes* (02C0203) in 14.2 gm CF-1 mixed mice.

Comments

Azithromycin and clarithromycin are both active against the susceptible *Streptococcus pyogenes* 02C0203. The outcomes for various lengths of therapy were compared in this infection model, because the peritonitis caused by this strain lends itself to prolonged therapy as 100% mortality doesn't occur until 2–3 days post-challenge. Clarithromycin was chosen as a comparator to azithromycin because the pharmacokinetics for these two macrolides are quite different. While clarithromycin achieves relatively high blood levels quickly and is cleared fairly rapidly, azithromycin accumulates in tissues and leeches out slowly over time into the bloodstream yielding overall lower blood levels than clarithromycin but a much longer exposure time. Additionally, the research of Craig et al. in preclinical species suggests that the outcomes observed with azithromycin best correlate with the PD parameter of the AUC/MIC and time above MIC for clarithromycin. See Craig, W. et al. (1997), "Postantibiotic effects and dosing of macrolides, azalides and streptogramins", in Expanding Indications of the New Macrolides, Azalides, and Streptogramins (Zinner S H, Young L S, Acar J F, Neu H C, eds.) pp. 27–38, Marcel Dekker, New York. This experiment was to determine if the compounds work better against a lung infection with *Streptococcus pyogenes* acute infection giving the same total therapeutic dose over a 1, 2, or 3-day dosing period. In this same type of experiment with a susceptible *Streptococcus pneumoniae* (02J 1016) it was found that azithromycin performs best when administered in one dose rather than spreading the same total dose out over 3 days. All three regimens of clarithromycin failed ($PD_5s > 200$ mg/kg), so no useful information was gleaned from that portion of the experiment except to say that when therapy was administered using a b.i.d. regimen the $PD_{50}s$ were in the range of 5–25 mg/kg.

Against 02C0203, azithromycin performs the best when given once rather than the total dose being spread out over 3 days. The azithromycin 1 day dosing $PD_5$ (1.0 mg/kg/regimen) is significantly different than the 2 and 3 day dosing $PD_{50}s$ (2.5 and 3.8 mg/kg/regimen, respectively). The 2 and 3 day dosing regimen $PD_{50}s$ are also significantly different from each other.

Clarithromycin has the best activity when given more often (2-days and 3-days dosing versus 1-day dosing). The $PD_{50}s$ for the 2 and 3-day dosing regimens (3.1 and 2.2 mg/kg/regimen) are equivalent, while the $PD_{50}$ for the 1-day dosing regimen, 11.3 mg/kg/regimen), is clearly higher. However, when the 95% confidence limits for all three regimens are taken into account, it appears as though all three regimens are equivalent. The 2 and 3-day therapies are more consistent with historical data for clarithromycin administered b.i.d. for 1-day.

Procedure

Azithromycin and clarithromycin were administered P.O. in diluent q.d. for either 1, 2 or 3 days after an I.P. challenge with *Streptococcus pyogenes* (02C0203) starting 1.0 hour after infection.

| Compound | Dose (mg/kg/day) | Mice Surviving/Total | PD50 (mg/kg/regimen) |
|---|---|---|---|
| Azithromycin P.O. | 12.5 | 10/10 | 3.8 (3.8–3.9)* |
| Lot #17419-64-IF | 3.12 | 10/10 | |
| MIC 0.01–0.10 µg/ml | 0.78 | 3/10 | |
| 3 day regimen | 0.20 | 0/10 | |
| Azithromycin P.O. | 25.0 | 9/10 | 2.5 (1.8–3.3) |
| Lot #17419-64-1F | 6.25 | 10/10 | |
| MIC 0.01–0.10 µg/ml | 1.56 | 7/10 | |
| 2 day regimen | 0.39 | 1/10 | |
| Azithromycin P.O. | 50.0 | 10/10 | 1.0 (0.6–1.4) |
| Lot #17419-64-1F | 12.5 | 10/10 | |
| MIC 0.01–0.10 µg/ml | 3.12 | 8/10 | |
| 1 day regimen | 0.78 | 3/10 | |
| Clarithromycin P.O. | 12.5 | 10/10 | 3.1 (2.6–3.7) |
| Lot #34844-174-01 | 3.12 | 9/10 | |
| MIC 0.01–0.03 µg/ml | 0.78 | 5/10 | |
| 3 day regimen | .20 | 0/10 | |
| Clarithromycin P.O. | 25.0 | 8/10 | 2.2 (0.9–3.6) |
| Lot #34844-174-01 | 6.25 | 9/10 | |
| MIC 0.01–0.03 µg/ml | 1.56 | 8/10 | |
| 2 day regimen | 0.39 | 0/10 | |
| Clarithromycin P.O. | 50.0 | 10/10 | 11.3 (3.1–19.4) |
| Lot #34844-174-01 | 12.5 | 6/10 | |
| MIC 0.01–0.03 µg/ml | 3.12 | 4/10 | |
| 1 day regimen | 0.78 | 0/10 | |
| Infected (non-treated) control | | | |
| 10-1 dilution | | 0/10 | |
| 10-2 dilution (used in study) | | 0/10 | |
| 10-3 dilution | | 0/10 | |
| BHI (non-infected control) | | 10/10 | |

*95% confidence limits
Bacterial challenge: $1 \times 10^6$ organisms/mouse

2.2.3 Murine Acute Infection Model Challenged with *Haemophilus influenzae*

Subject

Accelerated dosing paradigm. In vivo evaluation of azithromycin vs. an acute infection of *Haemophilus influenzae* 54A1100 (non-type B) in 20 gram [F] DBA/2 mice comparing equivalent therapies (same total therapeutic dose) administered over 1, 2 and 3 days. One set of clarithromycin-dosed mice was also tested, with total dose administered in just one day.

Discussion

Improved in vivo efficacy has been shown for azithromycin in preclinical infection models with *S. pneumoniae, S. pyogenes,* (both supra) and *Enterococcus faecalis* (infra) when the total therapeutic dose is administered in an accelerated fashion (one day of therapy vs. two or three). *Hemophilus influenzae* 54A1100 also produces a more slowly developing disease relative to more acutely lethal pathogens used in the in vivo models. Azithromycin had previously been tested in the mouse systematic disease (PD50) model utilizing a standard dosing paradigm (b.i.d. on day 1) and had a PD50 of 27 mg/kg. s.c. vs 54A1100. Because in this model 100% mortality is not seen until day 2 in the no drug controls, one is able to evaluate the influence of therapy duration on survival.

In this study, for azithromycin the same total therapeutic dose (i.e., 200 mg/kg/therapeutic regimen) was administered Q.D. on day one (i.e., 200 mg/kg on day 1), Q.D. on day one and two (i.e., 100 mg/kg on day 1 and 3) or Q.D. on day one, two and three (i.e., 67 mg/kg on day 1, 2 and 3). For azithromycin, efficacy was best with one therapeutic dose (25.3 mg/kg s.c.) and this accelerated dosing regimen was significantly better ($p<0.05$) than the 2 and 3-day regimens. Furthermore, the 2-day regimen was also significantly better than the 3-day regimen ($p<0.05$): Clarithromycin (with a one day dose regimen and an MIC of 8 μg/ml) failed (PD50: >200 mg/kg s.c.).

| Compound | Dose (mg/kg/day) | Mice Surviving/Total | PD50 (mg/kg/regimen) |
|---|---|---|---|
| Azithromycin s.c. | 200 | 10/10 | 25.3 (14.3–36.2)[1] |
| (17419-064-1F) | 50 | 9/10 | |
| MIC: 0.5–1 μg/ml | 12.5 | 1/10 | |
| Q.D. [1 day] | 3.12 | 0/10 | |
| Azithromycin | 100 | 10/10 | 49.9 (41.5–58.5) |
| (17419-64-1F) | 25 | 5/10 | |
| Q.D. [2 days] | 6.25 | 1/10 | |
| | 1.56 | 0/10 | |
| Azithromycin | 66.6 | 6/10 | 181.6 (180.1–183.1) |
| (17419-064-1F) | 16.6 | 0/10 | |
| Q.D. [3 days] | 4.15 | 0/10 | |
| | 1.04 | 0/10 | |
| Clarithromycin | 200 | 0/10 | >200 |
| (4844-174-01) | 50 | 2/10 | |
| MIC: 8 μg/ml | 12.5 | 0/10 | |
| Q.D. [1 day] | 3.12 | 0/10 | |
| Infected only dilution $10^{-2}$ | | 0/10 | |
| dilution $10^{-3}$ | | 0/10 | |
| dilution $10^{-4}$ | | 0/10 | |
| 3% yeast | | 10/10 | |

Bacterial challenge: $1 * 10^7$ per mouse
[1]95% confidence limits

2.2.4 Murine Acute Infection Model Challenged with *Enterococcus faecalis*

Subject

Accelerated dosing paradigm. In vivo evaluation of azithromycin and clarithromycin vs. an acute infection of *Enterococcus faecalis* 03A1085 in 22 gram [F] DBA/2 mice comparing equivalent therapies (same total therapeutic dose) administered over 1, 2 and 3 days.

Discussion

Previous experiments demonstrated improved in Vivo efficacy for azithromycin in preclinical infection models with *S. pneumoniae* and *S. pyogenes* (both supra) when the total therapeutic dose is administered in an accelerated fashion (one day of therapy vs. two or three). Azithromycin and clarithromycin are both active against the susceptible *Enterococcus faecalis* 03A1085 that also produces a more slowly developing disease relative to more acutely lethal pathogens used in the in vivo models. Azithromycin and clarithromycin had previously been tested in the mouse systemic disease (PD50) model utilizing a standard dosing paradigm (b.i.d. on day 1) and had PD50's of 10.1 mg/kg. s.c. and 1.7 mg/kg. s.c., respectively, vs. 03A1085. Because 100% mortality does not occur in this model until day 2–3 in the no drug controls, the experiment allows one to evaluate the influence of therapy duration on survival.

In this study, the same total therapeutic dose (i.e., 200 mg/kg/therapeutic regimen) was administered Q.D. on day one (i.e., 200 mg/kg on day 1), Q.D. on day one and two (i.e., 100 mg/kg on day 1 and 3) or Q.D. on day one, two and three (i.e., 67 mg/kg on day 1, 2 and 3). For azithromycin, efficacy was best with one dose (14.8 mg/kg s.c.) and this accelerated dosing regimen was significantly better ($p<0.05$). Interestingly, clarithromycin efficacy was also best with one dose (2/2 mg/kg s.c.), and as with azithromycin, the one-dose confidence limits did not overlap with the 2 and 3-day regimens. However, the data for the 2-day and 3-day regimens were indistinguishable.

| Compound | Dose (mg/kg/day) | Mice Surviving/Total | PD50 (mg/kg/regimen) |
|---|---|---|---|
| Azithromycin s.c. | 200 | 10/10 | 14.8 (10.2–19.5)[1] |
| (17419-064-1F) | 50 | 9/10 | |
| MIC: 3–6 μg/ml | 12.5 | 4/10 | |
| Q.D. [1 day] | 3.12 | 1/10 | |
| w/serum: 6.25 | | | |
| Azithromycin | 100 | 10/10 | 42.7 (42.2–43.2) |
| (17419-064-1F) | 25 | 7/10 | |
| Q.D. [2 days] | 6.25 | 0/10 | |
| | 1.56 | 1/10 | |
| Azithromycin | 66.6 | 9/10 | 59.3 (27.5–91.2) |
| (17419-064-1F) | 16.6 | 4/10 | |
| Q.D. [3 days] | 4.15 | 2/10 | |
| | 1.04 | 3/10 | |
| Clarithromycin | 100 | 10/10 | 2.2 (0.19–4.2) |
| (34844-174-01) | 25 | 10/10 | |
| MIC: 3.12 μg/ml | 6.25 | 7/10 | |
| Q.D. [1 day] | 1.56 | 3/10 | |
| w/serum: 3.12 | | | |
| Clarithromycin | 50 | 10/10 | 23.7 (5.4–42) |
| (34844-174-01) | 12.5 | 6/10 | |
| Q.D. [2 days] | 3.12 | 5/10 | |
| | 0.78 | 1/10 | |
| Clarithromycin | 33.3 | 9/10 | 2.2 (0.19–4.2) |
| (34844-174-01) | 8.3 | 8/10 | |
| Q.D. [3 days] | 2.08 | 1/10 | |
| | 0.52 | 3/10 | |
| Infected only dilution $10^{-2}$ | | 0/10 | 18.8 (7.2–30.3) |
| dilution $10^{-3}$ | | 1/10[2] | |
| dilution $10^{-4}$ | | 0/10 | |
| 3% yeast | | 10/10 | |

Bacterial challenge: $1 \times 10^7$ per mouse
[1]95% confidence limits
[2]PD50 adjusted

2.2.5 Accelerated Dosing Paradigm in the Gerbil Middle Ear Infection Model with Infection of *Haemophilus influenzae* 54A1100

Subject

Accelerated dosing paradigm in the gerbil middle ear infection model. In vivo evaluation of azithromycin vs. a localized infection of *Haemophilus influenzae* 54A1100 (non-type B) in 50.4 gram [F] Mongolian gerbils comparing one equivalent therapy [200 mg/kg/therapy p.o.] (same total therapeutic dose) administered over 1, 2, or 3 days. CFU counts/ml. bulla wash (5 gerbils per time point) were taken at 24, 48, 72, and 96 hours post-infection for each of the Q.D. 1, Q.D. 2, and Q.D. 3 groups.

Discussion

In this study based on a mg/kg/total regimen for azithromycin the same therapeutic dose (i.e., 200 mg/kg/therapeutic regimen) was administered Q.D. on day one (i.e., 200 mg/kg on day 1), Q.D. on day one and two (i.e., 100 mg/kg on day 1 and 2) or Q.D. on day. one, two and three (i.e., 66.6 mg/kg on day 1, 2 and 3). A baseline CFU count of bulla wash was measured 24 hours post-infection, before dosing began. Thereafter, samples for counts from each group were taken at 48, 72, 96 hours post-infection. By looking at the kinetics of bacterial reduction in the bulla wash, a kinetic kill curve could be constructed which was designed to visually elucidate the observed in vivo therapeutic efficacy by examining the dose/time-kill relationship (FIG. 3a).

Summary

In past studies of accelerated dosing with azithromycin vs. 54A1100 (in the gerbil), Q.D. 1, Q.D. 2, and Q.D. 3 therapies had equivalent activity (ED50's of 138.1, 138.1, and 162.7 mg/kg/total regimen, respectively). It did not matter if dosing began at 24 or 72 hours post-infection. This study indicates the importance of dose related (concentration) kill over time. For Q.D. 1, activity appeared to be cidal at the 200 mg/kg p.o. level (i.e., there was <log 2.0000 bacterial load at 48 hours post-infection (24 hours post-dose) and there was no re-growth at 72–96 hours post-infection). For Q.D. 2, at 48 hours post-infection (24 hours post-last-dose), cfu counts were reduced relative to infected control [P=0.0250] and eradication was observed in 4/5 test subjects at 72 hours post-infection (24 hours post-last-dose), P=0.0000, and at 96 hours post-infection (48 hours post-last-dose), P=0.0105. For Q.D. 3, at 48 hours post-infection (24 hours post-last-dose) bacterial reduction relative to infected control was not significant (P=0.8540) and while the bacterial burden was reduced at 72 and 96 hours post-infection, eradication was not observed in any test subject; 72 hours post-infection (24 hours post-last-dose), P=0.0007 and at 96 hours post-infection (24 hours post-last-dose), P=0.0902. The Q.D. 2 and Q.D. 3 therapies demonstrated antibacterial activity, but not total clearance and with possibly a slight regrowth by 96 hours post-infection (see graph below). In these two groups (in animals not cleared or $\geq$log 2.0000 cfu/ml bulla wash), concern for development of bacterial resistance arises because the bacterial load that is present is exposed to implicitly sub-therapeutic concentrations of antibiotic for the duration of the therapeutic evaluation (no susceptibilities were determined to address this point). Q.D. 1 at the 200 mg/kg p.o. level demonstrated the best activity with total clearance being demonstrated early on in therapy. This observation implies that the likelihood of development of resistance using this accelerated regimen would be diminished relative to the 2–3 day therapy.

| Compound | Dose (mg/kg/day) oral | Sample Time [hours] Post-Infection | Recoverable CFU (Bulla) [$Log_{10}$.Geo.Mean] (SEM) | P-value[2] |
|---|---|---|---|---|
| Azithromycin (17419-064-1F) Q.D. [1 day] | 200 | 24 | 7.3206 (0.28)[1] | |
| | | 48 | <2.0000 | P = .0000 |
| | | 72 | <2.0000 | P = .0001 |
| | | 96 | <2.0000 | P = .0001 |
| Azithromycin Q.D. 2 [2 days] Q.D. 2 (continued) | 100 | 24 | 7.3206 (0.28)[1] | |
| | | 48 | 5.7572 (0.54) | P = .0250 |
| | | 72 | <2.4580 (0.46) | P = .0000 |
| | | 96 | <3.1112 (1.11) | P = .0105 |
| Azithromycin Q.D. [3 days] | 66.6 | 24 | 7.3206 (0.28)[1] | |
| | | 48 | 5.8817 (0.44) | P = .8540 |
| | | 72 | 4.5981 (0.14) | P = .0007 |
| | | 96 | 6.1520 (0.75) | P = .0902 |
| Infected only | — | 24 | 7.3206 (0.28)[1] | |
| | | 48 | 7.2491 (0.26) | |
| | | 72 | 7.8242 (0.41) | |
| | | 96 | 7.7274 (0.33) | |

Bacterial challenge: 1 × 10[4]/gerbil
[1] 24 hours post-infection baseline count done before dosing begins (SEM)
[2] P-value: infected/dosed compared to infected only of same timepoint Summary: CFU Counts in Bulla Wash Samples at 48, 72, and 96 Hours Post Infection

| Group | Hrs. post Infection | Geo. Mean | SD | SEM | P-value [dosed to infected only of same timepoint group] |
|---|---|---|---|---|---|
| QD1 | 48 | <2.0000 | | | P = .0000 |
| QD2 | 48 | 5.7572 | 1.2 | 0.54 | P = .0250 |
| QD3 | 48 | 5.8817 | 0.99 | 0.44 | P = .8540 |
| Infected | 48 | 7.2491 | 0.57 | 0.26 | |
| QD1 | 72 | <2.0000 | | | P = .0001 |
| QD2 | 72 | <2.4580 | 1.02 | 0.46 | P = .0000 |
| QD3 | 72 | 4.5981 | 0.3 | 0.14 | P = .0007 |
| Infected | 72 | 7.8242 | 0.92 | 0.41 | |
| QD1 | 96 | <2.0000 | | | P = .0001 |
| QD2 | 96 | <3.1112 | 2.48 | 1.11 | P = .0105 |
| QD3 | 96 | 6.1520 | 1.67 | 0.75 | P = .0902 |
| Infected | 96 | 7.7274 | 0.73 | 0.33 | |

Note:
24 hour cfu counts (before dosing began): 7.3206 [log of cfu-bulla wash/ml]

2.26 Accelerated Dosing Paradigm in the Gerbil Middle Ear Infection Model with Infection of *Haemophilus influenzae* 54A1218

Subject

Accelerated dosing paradigm in the gerbil middle ear infection model. In vivo evaluation of azithromycin vs. a localized infection of *Haemophilus influenzae* 54A1218 (non-typeable/beta lactamase +) in 49.4 grams [F] Mongolian gerbils comparing one equivalent therapy [200 mg/kg/therapy p.o.] (some total therapeutic dose) administered over 1, 2, or 3 days. CFU counts/ml. bulla wash (5 gerbils per timepoint) were done at 24, 48, 72, and 96 hours post-infection for each of the Q.D. 1, Q.D. 2, and Q.D. 3 groups.

Discussion

In this study based on a mg/kg/total regimen for azithromycin, the same therapeutic dose (i.e., 200 mg/kg/therapeutic regimen) was administered Q.D. on day one (i.e., 200 mg/kg on day 1), Q.D. on day one and two (i.e., 100 mg/kg on day 1 and 2) or Q.D. on day one, two and three (i.e., 66.6 mg/kg on day 1, 2 and 3). A baseline CFU count of bulla wash was done 24 hours post-infection, before dosing began. Thereafter, samples for counts from each group were taken at 48, 72, 96 hours post-infection. By looking at the kinetics of bacterial reduction in the bulla wash, a kinetic kill curve could be constructed with the goal of visually showing the observed in vivo therapeutic efficacy by examining the dose/time-kill relationship (FIG. 3b).

Summary

In past studies of accelerated dosing with azithromycin vs. 54A1218 (in the gerbil), Q.D. 1, Q.D. 2, and Q.D. 3 therapies had equivalent activity (ED50's of 83.8 (53.6–114.1), 53.4 (21.2–85.5), and 65.2 (51–79.4) and 162.7 mg/kg/total regimen, respectively). This study indicates the importance of dose related (concentration) kill over time. For Q.D. 1, activity appeared to be cidal at the 200 mg/kg p.o. level (i.e., there was log <2.0602 bacterial load at 48 hours post-infection (24 hours post-dose) and there was no re-growth at 72–96 hours post-infection). For Q.D. 2, at 48 hours post-infection (24 hours post-last-dose), cfu counts were reduced relative to infected control [P=0.0338] and eradication was observed at 72 and 96 hours post-infection. For Q.D. 3, at 48 hours post-infection (24 hours post-last-dose) bacterial reduction relative to infected control was not significant (P=0.1889), but at 72 and 96 hours post-infection eradication was observed. Q.D. 1, Q.D. 2, and Q.D. 3 therapies were all effective at eradicating the organism by 72 hours post infection. Q.D. 1 at the 200 mg/kg p.o. level demonstrated the best activity with total clearance being demonstrated early on in therapy (48 hours post infection; 24 hours post-last-dose) and this observation implies that the likelihood of development of resistance using this accelerated regimen would be somewhat diminished relative to the 2–3 day therapy. These data are consistent with the results that were observed vs. strain 54A1100 (non-type B *H. influenzae*) except that there is eradication with all azithromycin regimens by 72 hours post-challenge with this strain.

| Compound | Dose (mg/kg/day) oral | Sample Time [hours] Post-Infection | Recoverable CFU (Bulla) [Log$_{10}$.Geo.Mean] (SEM) | P-value[2] |
|---|---|---|---|---|
| Azithromycin s.c. (17419-064-1F) Q.D. [1 day] | 200 | 24 | 7.7206 (0.15)[1] | |
| | | 48 | <2.0000 | P = .0000 |
| | | 72 | <2.0602 | P = .0000 |
| | | 96 | <2.0000 | P = .0000 |
| Azithromycin Q.D. 2 [2 days] Q.D. 2 (continued) | 100 | 24 | 7.7206 (0.15)[1] | |
| | | 48 | <3.8587 (1.04) | P = .0338 |
| | | 72 | <2.0000 | P = .0001 |
| | | 96 | <2.0000 | P = .0000 |
| Azithromycin Q.D. [3 days] | 66.6 | 24 | 7.7206 (0.15)[1] | |
| | | 48 | <5.2399 (1.21) | P = .1889 |
| | | 72 | <2.0000 | P = .0001 |
| | | 96 | <2.0000 | P = .0000 |
| Infected only | — | 24 | 7.7206 (0.15)[1] | |
| | | 48 | 7.1691 (0.09) | |
| | | 72 | 7.7736 (0.2)[3] | |
| | | 96 | 7.7274 (0.33) | |

Bacterial challenge: 1.2 × 10[6]/gerbil
[1]24 hours post-infection baseline count done before dosing begins (SEM)
[2]P-value: infected/dosed compared to infected only of same timepoint
[3]There were four gerbil samples in this group; all other groups had five samples/group

| Group | Hours Post Infection | Geo. Mean | % Clearance of Group | SD | SEM | P-value [dosed to infected only of same timepoint group] |
|---|---|---|---|---|---|---|
| QD1 | 48 | <2.0000 | 100% | | | P = .0000 |
| QD2 | 48 | <3.857 | 40% | 2.32 | 1.04 | P = .0338 |
| QD3 | 48 | <5.2399 | 40% | 2.71 | 1.21 | P = .1889 |
| Infected | 48 | 7.1691 | 0% | 0.22 | 0.098 | |
| QD1 | 72 | <2.0602 | 100% | 0.13 | 0.06 | p = .0000 |
| QD2 | 72 | <2.0000 | 100% | | | P = .0001 |
| QD3 | 72 | <2.0000 | 100% | | | P = .0001 |
| Infected | 72 | 7.7736** | 0% | 0.39 | 0.2 | |
| QD1 | 96 | <2.0000 | 100% | | | P = .0000 |
| QD2 | 96 | <2.0000 | 100% | | | P = .0000 |
| QD3 | 96 | <2.0000 | 100% | | | P = .0000 |
| Infected | 96 | 7.4296 | 0% | 0.51 | 0.23 | |

Note:
24 hour cfu counts (before dosing began): 7.7206 [log of cfu-bulla wash/ml]
<1 × 10[3] cfu/ml considered negative;
≥1 × 10[3] considered positive
**4 samples in this group; all others had 5 samples 2.2.7 Accelerated Dosing of Azithromycin in Preclinical Models The results from the following study show the comparative in vivo activity of azithromycin following one-, two-, and three-day dosing regimens in preclinical species infection models. The localized gerbil otitis media model was utilized to evaluate the in vivo kill kinetics of azithromycin using these three dosing regimens. Additionally, the serum and pulmonary tissue pharmacokinetics of azithromycin in mice were characterized for the three dosing intervals.

Materials and Methods

MIC Determinations. *Streptococcus pneumoniae, S. pyogenes, E. faecalis,* and *H. influenzae* MICs were determined using the broth microdilution procedure recommended by the NCCLS. Test trays were incubated at 35 C. without carbon dioxide. For testing of streptococci, the cation-adjusted Mueller-Hinton broth was supplemented with 2–3% lysed horse blood. For testing *H. influenzae,* freshly prepared *Haemophilus* Test Medium broth was used.

Bacterial Strains.
- *S. pneumoniae* 02J1016, serotype 3, originally isolated from blood culture (strain P 4241) (MLS- and penicillin-susceptible).
- *S. pyogenes* 02C0203, ATCC 12384, group A, type 3 (MLS-susceptible).
- *E. faecalis* 03A1085, vancomycin susceptible clinically derived strain.
- *H. influenzae* 54A1100, (43095 ATCC Fulghum strain) non-serotype B strain originally isolated from otitis media (macrolide and penicillin susceptible).
- *H. influenzae* 54A1218, clinically derived non-serotype B strain (macrolide-susceptible, penicillin-resistant, TEM-1 beta-lactamase).

Animals.
Female Swiss (CF-1) mice, 5–6 weeks of age (18–20 g): *S. pneumoniae/pyogenes.*
Female DBA/2 mice, 5–6 weeks of age (18–20 g): *H. influenzae.*
Female Mongolian gerbils, 6–7 weeks of age (45–50 g): *H. influenzae.*

Models of Infection.
Peritonitis Model: Mice were infected intraperitoneally with a 10 $LD_{100}$ inoculum of the culture. With enterococcal and haemophilus strains, the inoculum was fortified with 3% Brewers yeast as a bacterial enhancing adjuvant. Oral therapy was initiated at 0.5 after the bacterial challenge (n=30 mice per dose level) and administered QD over one, two, and three days (same total therapeutic dose administered over different dosing intervals). Survivors were recorded over 7 days at which time $ED_{50}$s were determined from the survival data at day five using non-linear regression techniques.

*S. pneumoniae* pneumonia model: Mice were infected intranasally with an $LD_{100}$ inoculum of a log phase pneumococcal culture (about $10^4$ CFU per mouse). Oral therapy was initiated at 18 h following bacterial challenge and was administered QD for one, two, or three days (n=30 mice per dose level). Survivors were recorded for 10 days at which time $ED_{50}$s were determined from the survival data at day ten using the nonlinear regression techniques.

*H. influenzae* therapeutic model: Gerbils were infected with about $10^{3-4}$ CFU of *H. influenzae* via intra-bulla instillation. Oral therapy was initiated 18 h following challenge and consisted of QD dosing for 1, 2, and 3 days (n=10 gerbils per dose level). Bulla were tapped, washed with 100 microliter of saline and recoverable *H. flu* enumerated (limit of detection was 100 CFU). $ED_{50}$ values were estimated from the clearance data (% of animals that cleared the *H. flu* culture) over the evaluated dosage range.

*H. influenzae* in vivo time kill: Gerbils were infected with about $10^{3-4}$ CFU of *H. flu* via intrabulla instillation. Oral therapy was initiated 24 h following challenge and consisted of QD dosing of 200 mg/kg for one, two, and three days with the same total therapeutic dose being administered to each group (n=5). Bulla were tapped at 24, 48, 72 and 96 hours following challenge, washed with saline and recoverable *H. flu* enumerated (limit of detection was 100 CFU).

Pharmacokinetics.

Female CF-1 mice were orally administered azithromycin at 100 mg/kg QD for one day, 50 mg/kg QD for two days and 33 mg/kg QD for three days. Azithromycin was formulated in a 0.5% methylcellulose vehicle. Blood and pulmonary tissue samples were taken starting at 0.5 h post-dose and at predetermined intervals over a 96 h period. Plasma and lung samples were prepared and maintained at -70 C. Plasma and pulmonary tissue concentrations of azithromycin were determined by a non-validated LC/MS assay using Turbo Ion-Spray mass spectrometry detection. The lower limit of quantification (LLOQ) was 50 ng/ml. The upper limit of quantification (ULOQ) was 1.25 µg/ml. Interassay variability was <7%. Pharmacokinetic parameters were calculated using the non-compartmental method by WinNonlin 2.1 (Scientific Consulting, Inc.).

Results

In peritonitis models, bacterial strains were chosen on their ability to produce a more chronic disease (time to mortality in infected controls was 2–3 days) so that prolonged therapy could be evaluated. Against isolates of *S. pyogenes, S. pneumoniae, E. faecalis* and *H. influenzae,* a one-day QD therapeutic regimen of azithromycin was superior to a two- and/or three-day QD regimen (Table 5). Comparison of similar dosing regimens with clarithromycin was equivocal.

TABLE 5

INFLUENCE OF DOSING REGIMEN ON THE THERAPEUTIC ACTIVITY OF AZITHROMYCIN AND CLARITHROMYCIN IN MURINE PERITONITIS MODELS

| | | $ED_{50}$ values for various dosing regimens | | |
|---|---|---|---|---|
| Drug | MIC (µg/ml) | One-Day Therapy (mg/kg/therapy) | Two-Day Therapy (mg/kg/therapy) | Three-Day Therapy (mg/kg/therapy) |
| *Streptococcus pyogenes* 02C0203 | | | | |
| Azithromycin | 0.03 | 0.78[1] | 1.1 | 1.25 |
| Clarithromycin | 0.03 | 11.7[1] | 2.5 | 3.8 |
| *Streptococcus pneumoniae* 02J1016 | | | | |
| Azithromycin | 0.10 | 8.7[1] | 7.6 | 15.1 |
| Clarithromycin | 0.05 | 99.8 | 103.0 | 87.5 |
| *Enterococcus faecalis* 03A1085 | | | | |
| Azithromycin | 6.25 | 12.7[1] | 44.5 | 44.4 |
| Clarithromycin | 3.12 | 6.1 | 16.6 | 23.1 |
| *Haemophilus influenzae* 54A1100 | | | | |
| Azithromycin | 1.56 | 30.3[1] | 48 | 147 |
| Clarithromycin | 8 | >200 | >200 | >200 |

[1] Indicates that One-Day therapy $ED_{50}$ value is significantly different from two- and/or three-day therapies Similarly, in a murine pneumococcal pneumonia model one-day azithromycin therapy was superior to the three-day regimen (Table 6). For clarithromycin, the dosing regimen did not impact outcome, as the $ED_{50}$ values were comparable regardless of dosing interval. QD dosing of clarithromycin is suboptimal in this model.

TABLE 6

INFLUENCE OF DOSING REGIMEN ON THE THERAPEUTIC ACTIVITY OF AZITHROMYCIN AND CLARITHROMYCIN IN A MURINE PNEUMONIA MODEL

| | | $ED_{50}$ values for various dosing regimens | | |
|---|---|---|---|---|
| Drug | MIC (μg/ml) | One-Day Therapy (mg/kg/ therapy) | Two-Day Therapy (mg/kg/ therapy) | Three-Day Therapy (mg/kg/ therapy) |
| *Streptococcus pneumoniae* 02J1016 | | | | |
| Azithromycin | 0.10 | 20[1] | 27 | 49 |
| Clarithromycin | 0.05 | 270 | 327 | 338 |

[1] Indicates that One-Day therapy $ED_{50}$ value is significantly different from two- and/or three-day therapies The length of therapy did not have an impact on the therapeutic activity of azithromycin against two non-type B strains of *H. influenzae* in the gerbil otitis media infection model (see Table 7). Because the gerbil does not metabolize clarithromycin to 14-hydroxyclarithromycin and dosing of clarithromycin was not optimized, clarithromycin failed in this model. Although the results for Augmentin® amoxicillin/clavulanate potassium (manufactured by GlaxoSmithKline, Inc.) show that the absolute $ED_{50}$ using the three-day regimen was lower than for the two- or one-day regimens, this was not statistically significant.

TABLE 7

INFLUENCE OF DOSING REGIMEN ON THE THERAPEUTIC ACTIVITY OF AZITHROMYCIN AND COMPARATOR IN GERBIL OTITIS MEDIA MODELS

| | | $ED_{50}$ values for various dosing regimens | | |
|---|---|---|---|---|
| Drug | MIC (μg/ml) | One-Day Therapy (mg/kg/ therapy) | Two-Day Therapy (mg/kg/ therapy) | Three-Day Therapy (mg/kg/ therapy) |
| *Haemophilus influenzae* 54A1100 | | | | |
| Azithromycin | 1.56 | 138 | 138 | 163 |
| Clarithromycin | 8 | >200 | >200 | >200 |
| *Haemophilus influenzae* 54A1218 | | | | |
| Azithromycin | 0.78 | 84 | 53 | 65 |
| Augmentin | 1 | 72 | 100 | 55 |

Figure 4:
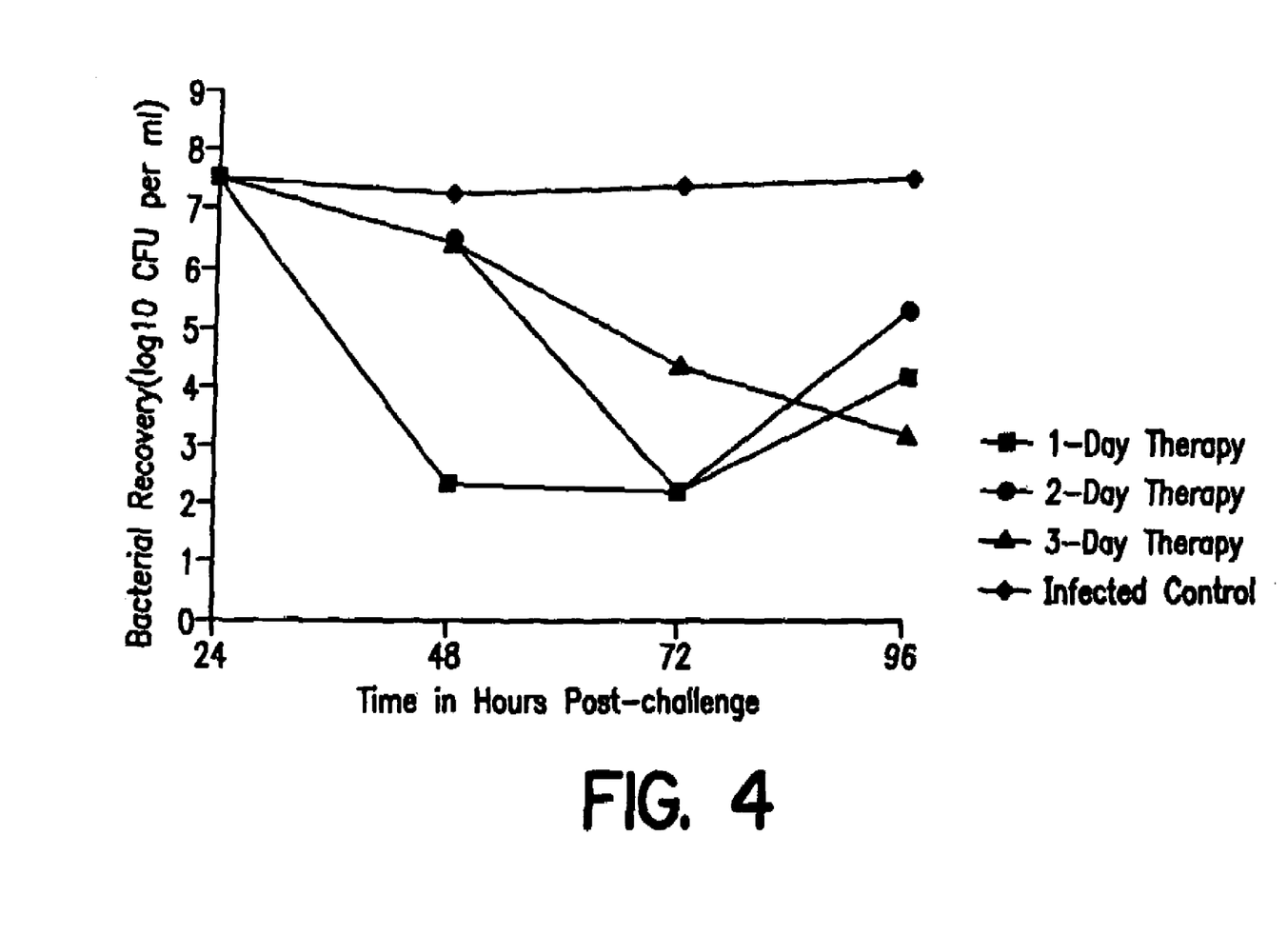
FIG. 4 shows the impact of different dosage regimens of Augmentin® amoxicillin/clavulanate potassium (from GlaxoSmithKline, Inc.) on an infection of *H. influenzae* in a gerbil model of middle ear infection.

The in vivo kill kinetics for azithromycin (200 mg/kg/ therapy) against a penicillin-susceptible *H. influenzae* strain suggest that one-day therapy rapidly eradicates the pathogen while extended therapies do not clear the pathogen (FIG. 3). Against a penicillin-resistant *H. influenzae* isolate a similar profile was observed with a more rapid eradication using the one-day therapy (FIG. 3). In contrast, Augmentin® amoxicillin/clavulanate potassium (manufactured by GlaxoSmithKline, Inc.) rapidly killed the pathogen with the one-day regimen. The three-day regimen, however, resulted in improved persistent effects relative to the one-day and two-day regimens (see FIG. 4).

Figure 5:
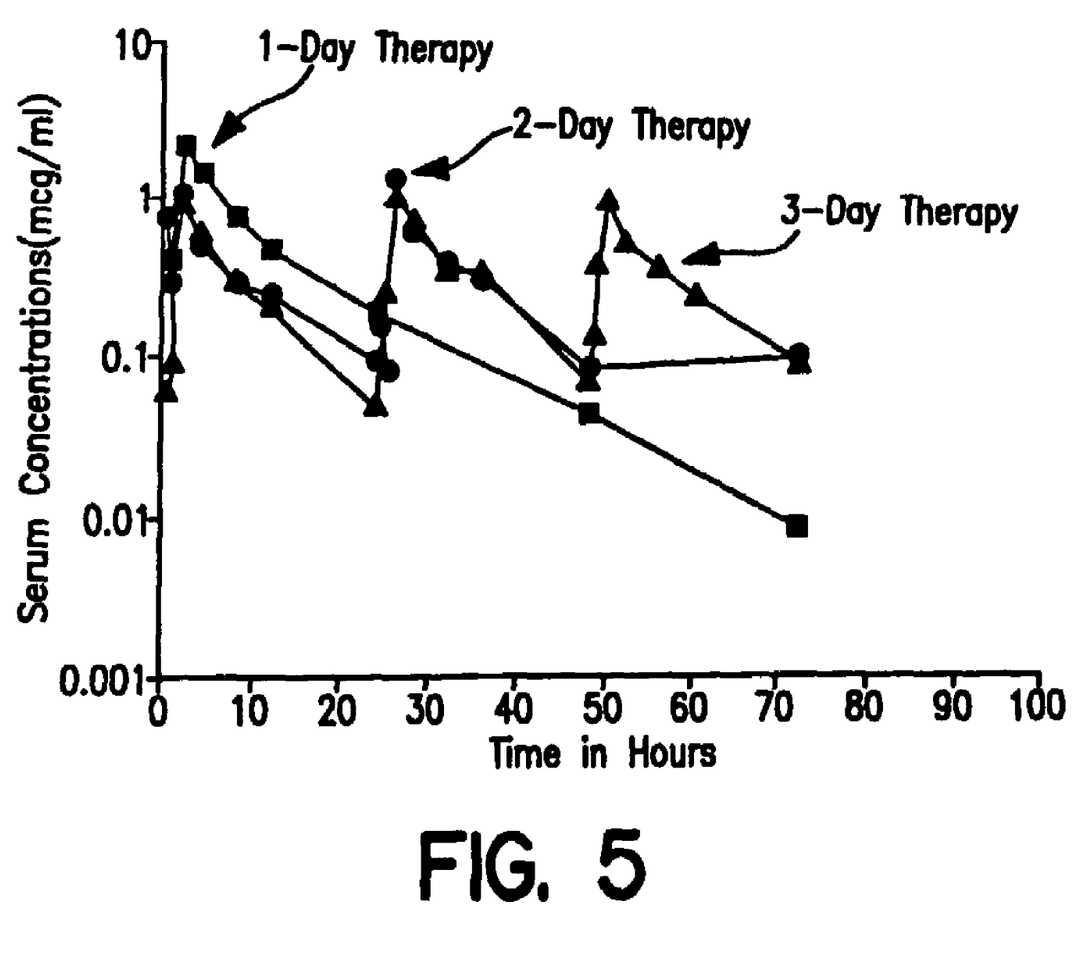
FIG. 5 shows azithromycin mouse serum concentrations following dosage of azithromycin administered over one, two or three days.

The serum and pulmonary tissue pharmacokinetics of azithromycin were characterized at a total dose of 100 mg/kg dose administered over one, two, and three days (Table 8 and FIG. 5). The serum and pulmonary tissue exposures are independent of dosing regimen. $T_{max}$ varies significantly. $C_{max}$ is dependent on the dosing interval with the one-day regimen resulting in the highest $C_{max}$.

TABLE 8

COMPARISON OF AZITHROMYCIN SERUM AND PULMONARY PK PARAMETERS FOLLOWING A TOTAL DOSE OF 100 MG/KG ADMINISTERED QD OVER 1, 2 AND 3 DAYS

| Total Dose (mg/kg) | Days of Dosing | Individual Dose (mg/kg/dose) | $C_{max}$ (mcg/ml) | $T_{max}$ (hr) | $AUC_{(0-)}$ (mcg * h/ml) |
|---|---|---|---|---|---|
| Serum PK | | | | | |
| 100 | 1 | 100 | 2.1 | 2 | 18.8 |
| 100 | 2 | 50 | 1.3 | 26 | 15.9 |
| 100 | 3 | 33.3 | 0.98 | 26 | 19.8 |
| Pulmonary PK | | | | | |
| 100 | 1 | 100 | 40 | 4 | 970 |
| 100 | 2 | 50 | 31 | 28 | 870 |
| 100 | 3 | 33.3 | 28 | 12 | 1048 |

In sum, these results show the relative efficacy of one-, two- and three-day dosing regimens of azithromycin in three preclinical infection models using primarily relevant bacterial pathogens. These efficacy data indicate that a one-day dosing regimen is better or at the very least equivalent to a longer course of therapy. The pharmacokinetics of azithromycin is consistent with the observed pharmacodynamics in these models. Additionally, the in vivo kill kinetics of azithromycin against *H. influenzae* suggest that bacterial clearance is more rapid with a one-day dosing regimen. This attribute may have benefits in suppressing the emergence of resistant strains. In sum, these preclinical infection model data correspond with the clinical studies supporting the advantages of one-day therapy over a more prolonged course of therapy.

2.3 Macrolide Resistance Studies in Humans

The results from two in vivo human studies for otitis media are summarized in view of the resistance data they provide. Relevant features of the testing are summarized also.

2.3.1 Human Studies: Antimicrobial Susceptibility Testing

Cultures were taken for antimicrobial susceptibility testing and bacterial species were identified. Current NCCLS approved breakpoints for MICs and zone sizes were applied to all data irrespective of the breakpoint in use at the time of the study. The isolates from the clinical studies were sent to central laboratories for identification and susceptibility determination. The methods for agar diffusion disk tests are those recommended by NCCLS.

The susceptibility breakpoints for azithromycin were defined as follows:

| | Susceptible | | Intermediate | | Resistant | |
|---|---|---|---|---|---|---|
| Pathogen | MIC | Zone Diameter | MIC | Zone Diameter | MIC | Zone Diameter |
| *Streptococcus* | ≦0.5 | ≧18 | 1 | 14–17 | ≧2 | ≦13 |
| *H. influenzae* | ≦4 | ≧12 | * | * | * | * |
| *M. catarrhalis* | ≦2 | ≧18 | 4 | 14–17 | ≧8 | ≦13 |

MIC (μg/ml);
Zone diameter (mm);
*Current absence of data on resistant strains precludes defining any resistant categories other than "susceptible" for azithromycin.

2.3.2 Human Studies: Otitis Media Studies 2.3.2.1 Study A0661015

This was a non-comparative trial using a single 30 mg/kg dose of azithromycin in the treatment of otitis media in pediatric subjects undergoing diagnostic tympanocentesis. Overall the MITT analysis of bacteriological response included 113 subjects. Thirty-nine strains of *H. influenzae* were able to be evaluated for bacteriologic outcome and were susceptible as defined by NCCLS criteria. The clinical failure (and presumed persistence) rate was 33.3%. Historically, *H. influenzae* as the causative pathogen in otitis media has been difficult to treat as evidenced by the clinical cure rates in package inserts for other antibiotics (see Table below). The latter is true for multiple antibiotics, despite the organism being susceptible to the antibiotic. Not all strains are equally virulent and the growth rate and kinetics of infection may influence the outcome. In addition, *H. influenzae* has been a difficult organism to culture from the middle ear. The use of PCR primers specific for this organism (and others) has been shown to have detection limits equivalent to 6–7 organisms and to be 85% concordant with traditional culture methods with no false positives. The protocol was further validated by using reverse transcriptase-polymerase chain reaction to detect the presence of bacterial mRNA in a significant percentage of culturally sterile middle ear effusions, thereby establishing the presence of viable, metabolically active, intact organisms in patients with otitis media with effusion that are culture-negative. Using this methodology, seventeen additional patients were identified as having an *H. influenzae* strain at baseline by PCR analysis; all were deemed clinically cured at the test of cure (TOC) end point. If these *H. influenzae* cures are added into the total, the clinical cure rate increases to 76.8% overall.

*pneumoniae* isolates (MICs≦0.25 µg/ml) was 92.5% and 66.7% versus resistant isolates. Of note, 40% of strains with MIC values of >256 µg/ml were clinically cured. The one failure that occurred in the group of pneumococcal strains with an MIC of 8 µg/ml was a patient that was coinfected with *H. influenzae* at baseline. On day 4 a culture was taken from the opposite ear of this patient yielding a clonally distinct *S. pneumoniae* strain with high level resistance to both azithromycin and clindamycin (MIC>256 and >128 µg/ml respectively; see below). The evaluation of the left ear by the clinician at this time found that ear pain and ear fullness decreased and there was increased hearing in the left ear. In addition, the acoustic reflectometry on the left ear had improved by day 4. Thus, it appeared that the ear with initial *S. pneumoniae* isolate (MIC to azithromycin of 8 µg/ml) could be counted as clinically cured and that the *H. influenzae* co-infection may also have been resolved. On the same day, this patient was started on amoxicillin/clavulanic add therapy; however, this patient's response was assessed as a failure at both EOT and TOC. It is likely that this failure resulted from nonresolution of the pneumococcal isolate harboring erm(B) (see below). If one corrects for this patient by ascribing the failure to the >256 µg/ml category, the cure rates become 7/7 for strains with an efflux mechanism of resistance and 2/6 for strains with a ribosome methylation mechanism of resistance. Although the numbers are small and eradication is presumed, the cure rate observed for strains harboring an efflux versus a methylase gene agrees with observations made in recent publications.

PCR determination of resistance mechanism in all the azithromycin-resistant pneumococci was done by previously published methods. All the strains with an azithromycin MIC of >256 µg/ml and a clindamycin MIC of 128 or >256 µg/ml had the erm(B) resistance determinant. All strains

*H. influenzae* Historical Response Rates to Other Antibiotics

| Primary Antibiotic | Response | Comparator | Response | Endpoint |
| --- | --- | --- | --- | --- |
| Azithromycin (1015) | 28/44 (64%) | N/A | N/A | Clinical cure at TOC visit (day 24–28) |
| Azithromycin (historical) | 30/47 (64%) | N/A | N/A | Presumptive bacterial/clinical cure outcomes (i.e., clinical success) at day 30 |
| Cefpodoxime proxetil | 50/76 (66%) | Cefixime | 61/81 (75%) | Presumptive bacterial/clinical success outcomes (i.e., cured and improved) at 4–21 day post-therapy follow-up |
| Clarithromycin | 10/14 (71%) | Oral Cephalosporin | 3/4 (75%) | Presumptive bacterial/clinical eradication/clinical cure outcomes (i.e., clinical success) post-therapy |
| Ceftriaxone | 22/31 (71%) | N/A | N/A | Bacteriological eradication rates at study day 30 + 2 |
| Cefprozil | 17% less than control (amoxicillin/clavulanic acid) cefprozil success rate | | | Presumptive bacterial/clinical cure outcomes (i.e., clinical success) at 10–16 days post-therapy |

Source: Data herein and 2000 Physicians' Desk Reference;
N/A = Not Applicable

All *M. catarrhalis* (10 isolates) were susceptible to azithromycin and clinically cured at TOC.

For pneumococcal isolates for which MIC values were determined, the clinical cure rate versus susceptible *S.* with an azithromycin MIC of 8 µg/ml and a clindamycin MIC of ≦0.06 µg/ml were confirmed as mef(A). Other resistance mechanisms such as esterases [(ere(A), ere(B)], phosphotransferases [mph(A), mph(B), mph(C)] or other erm classes [erm(A)—including erm(TR) subclass, erm(C)] were not detected. Mutations in 23S rRNA or ribosomal proteins L4 and L22 were not determined.

The one patient mentioned above that harbored a strain with the efflux determinant at ay 1 was a clinical failure at TOC. However, the failure appears to be the result of infection and survival by another *S. pneumoniae* isolate. When the isolates, 0067-base and −67-Ubase.1 (day 4), were examined by pulse-field gel electrophoresis, they were found to be clonally distinct. Additionally, the initial *S. pneumoniae* isolate, 0067-base, was mef(A) by PCR analysis, while the second isolate, 0067-Ubase.1, was an isolate from the opposite ear and contained a different *S. pneumoniae* isolate with an erm(B) determinant.

The agreement in susceptibility interpretation, MIC versus Zone Size, was 100% for all species isolated. That is, a strain having a resistant MIC always had a resistant Zone Size and the same was true for susceptible strains. No intermediate values were observed. This data is consistent with the current breakpoints for zone size and correlates well with MIC values. Given the recent discussions around the lack of correlation between clinical cures and in vitro susceptibility breakpoints, it would seem prudent to consider that seven of the seven pneumococci harboring mef(A) at baseline were clinical cures-by TOC. All of these isolates had an azithromycin MIC of 8 µg/ml.

2.3.2.2 Study 95–001

In this study, both a single dose (30 mg/kg) and 3-day regimen of azithromycin (10 mg/kg/day for 3 days) were compared to a single intramuscular dose of ceftriaxone (50 mg/kg). Specimens for culture and susceptibility testing were obtained from the infected ear by tympanocentesis within 24 h of start of therapy. Susceptibility to azithromycin and ceftriaxone was evaluated by Kirby-Bauer disk diffusion assays following the 1993 NCCLS guidelines. However, the study was evaluated using the breakpoints in the most recent set of guidelines.

To be a bacteriological cure, the MITT subject had to have a positive culture from the middle ear for *S. pneumoniae, H influenzae,* or *M. catarrhalis.* Eradication was defined as presumed eradication of pretreatment pathogen(s) based on signs/symptoms or unavailability of culturable material. All evaluable patients had only one of the bacterial species present at baseline. There was no bacteriological response data collected for 95-001. However, the clinical outcome by bacterial pathogen at follow-up (approximately 28 days after first visit) was collected. For patients with *S. pneumoniae* as the baseline pathogen, all treatment arms yielded 100% clinical cure when the investigators' evaluations that were missing are not included in the analysis. There were few *M catarthalis* strains isolated for any treatment arm but the two isolates observed in the 3-day dosing regimen of azithromycin were presumed bacteriological cures at follow-up. In otitis media caused by *H. influenzae,* there was 1 failure in 8 patients and 2 failures in 13 patients in the single dose and 3-day regimens of azithromycin, respectively. The comparator drug, ceftriaxone, had no failures out of 9 patients.

All *H. influenzae* organisms isolated were susceptible to azithromycin by agar diffusion (zone size), giving zone sizes of >19 mm with azithromycin and therefore susceptible according to the NCCLS breakpoint of >12 mm. Approximately 80% of the *S. pneumoniae* isolates were susceptible by MIC analysis whereas 15.7% of the strains had intermediate resistance and 3.5% were fully resistant. Of the nine patients with *S. pneumoniae* isolates with intermediate resistance, five were in one of the azithromycin regimens. All had clinical outcomes of either "cure" or "improvement" at EOT or follow-up. Even the highly macrolide-resistant isolate (MIC=256 µg/ml) was assessed a clinical cure at follow-up. Both dosing schedules of azithromycin were equivalent to the comparator, ceftriaxone.

The invention claimed is:

1. A method of treating an acute otitis media infection in a human comprising administering to a human in need thereof a single dose of azithromycin wherein the dose is between about 30 mg/kg and about 90 mg/kg body weight; wherein the acute otitis media is caused by an *S. pneumoniae* isolate containing a mef A gene.

2. The method of claim 1 wherein the dose is between about 30 mg/kg and 85 mg/kg body weight.

3. The method of claim 1 wherein the dose is between about 30 mg/kg and 80 mg/kg body weight.

4. The method of claim 1 wherein the dose is between about 30 mg/kg and 75 mg/kg body weight.

5. The method of claim 1 wherein the dose is between about 30 mg/kg and 70 mg/kg body weight.

6. The method of claim 1 wherein the dose is between about 30 mg/kg and 65 mg/kg body weight.

7. The method of claim 1 wherein the dose is between about 30 mg/kg and 60 mg/kg body weight.

8. The method of claim 1 wherein the dose is between about 30 mg/kg and 55 mg/kg body weight.

9. The method of claim 1 wherein the dose is between about 30 mg/kg and 50 mg/kg body weight.

10. The method of claim 1 wherein the dose is between about 30 mg/kg and 45 mg/kg body weight.

11. The method of claim 1 wherein the dose is between about 30 mg/kg and 40 mg/kg body weight.

12. The method of claim 1 wherein the human is an adult sixteen years of age or older.

13. The method of claim 1 wherein the human is a child under sixteen years of age.

14. The method of claim 1 wherein the human is a child twelve years of age or younger.

15. A method of treating acute otitis media in a human comprising administering to a human in need thereof a single dose of azithromycin wherein the dose is within the range of about 1.5 to 4.5 g; wherein the acute otitis media is caused by an *S. pneumoniae* isolate containing a mef A gene.

16. The method of claim 15 wherein the dose is within the range of about 1.5 to 2.5 g.

17. The method of claim 15 wherein the dose is within the range of about 2.5 to 3.5 g.

18. The method of claim 15 wherein the human is an adult sixteen years of age or older.

* * * * *